(12) United States Patent
Macdonald et al.

(10) Patent No.: US 11,224,208 B2
(45) Date of Patent: *Jan. 18, 2022

(54) GENETICALLY MODIFIED MAJOR HISTOCOMPATIBILITY COMPLEX MICE

(71) Applicant: REGENERON PHARMACEUTICALS, INC., Tarrytown, NY (US)

(72) Inventors: Lynn Macdonald, Harrison, NY (US); Andrew J. Murphy, Croton-on-Hudson, NY (US); Vera Voronina, Sleepy Hollow, NY (US); Cagan Gurer, Chappaqua, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/184,473

(22) Filed: Nov. 8, 2018

(65) Prior Publication Data

US 2019/0133095 A1   May 9, 2019

Related U.S. Application Data

(63) Continuation of application No. 14/185,316, filed on Feb. 20, 2014, now Pat. No. 10,154,658.

(60) Provisional application No. 61/767,811, filed on Feb. 22, 2013.

(51) Int. Cl.
| | |
|---|---|
| *A01K 67/027* | (2006.01) |
| *C07K 14/74* | (2006.01) |
| *C07K 14/73* | (2006.01) |
| *C07K 14/705* | (2006.01) |
| *C12N 15/85* | (2006.01) |

(52) U.S. Cl.
CPC .... *A01K 67/0278* (2013.01); *C07K 14/70539* (2013.01); *A01K 2207/15* (2013.01); *A01K 2217/072* (2013.01); *A01K 2267/03* (2013.01); *C07K 14/70514* (2013.01); *C07K 14/70517* (2013.01); *C12N 15/8509* (2013.01)

(58) Field of Classification Search
CPC .................................................. A01K 67/0278
See application file for complete search history.

(56) References Cited

U.S. PATENT DOCUMENTS

| | | | |
|---|---|---|---|
| 5,413,923 A | 5/1995 | Kucherlapati et al. | |
| 5,416,260 A | 5/1995 | Koller et al. | |
| 5,574,205 A | 11/1996 | Kucherlapati et al. | |
| 5,644,065 A | 7/1997 | Benoist et al. | |
| 5,859,312 A | 1/1999 | Littman et al. | |
| 5,942,435 A | 8/1999 | Wheeler | |
| 5,965,787 A | 10/1999 | Luthra et al. | |
| 6,002,066 A | 12/1999 | Leung et al. | |
| 6,139,835 A | 10/2000 | Kucherlapati et al. | |
| 6,150,584 A | 11/2000 | Kucherlapati et al. | |
| 6,270,772 B1 | 8/2001 | Burrows et al. | |
| 6,372,955 B1 | 4/2002 | Karlsson et al. | |
| 6,514,752 B1 | 2/2003 | Kucherlapati et al. | |
| 6,586,251 B2 | 7/2003 | Economides et al. | |
| 6,596,541 B2 | 7/2003 | Murphy et al. | |
| 6,815,171 B2 | 11/2004 | Burrows et al. | |
| 7,105,348 B2 | 9/2006 | Murphy et al. | |
| 7,265,218 B2 | 9/2007 | Burrows et al. | |
| 7,294,754 B2 | 11/2007 | Poueymirou et al. | |
| 7,339,089 B2 | 3/2008 | Gotch | |
| 7,663,017 B2 | 2/2010 | Lone et al. | |
| 7,745,690 B2 | 6/2010 | Kanazawa et al. | |
| 8,178,653 B2 | 5/2012 | Tureci et al. | |
| 8,847,005 B2 | 9/2014 | Macdonald et al. | |
| 9,043,996 B2 | 6/2015 | Macdonald et al. | |
| 9,585,373 B2 | 3/2017 | Macdonald et al. | |
| 9,591,835 B2 | 3/2017 | Macdonald et al. | |
| 9,615,550 B2 | 4/2017 | Macdonald et al. | |
| 10,154,658 B2 * | 12/2018 | MacDonald | C07K 14/70539 |
| 2002/0164721 A1 | 11/2002 | Firat et al. | |
| 2003/0093818 A1 | 5/2003 | Belmont et al. | |
| 2003/0124524 A1 | 7/2003 | Kornman et al. | |
| 2004/0137537 A1 | 7/2004 | Montero-Julian et al. | |
| 2005/0050580 A1 | 3/2005 | Gotch et al. | |
| 2005/0066375 A1 | 3/2005 | Thiam et al. | |

(Continued)

FOREIGN PATENT DOCUMENTS

| | | |
|---|---|---|
| EP | 0437576 B1 | 7/2002 |
| EP | 1878342 A1 | 1/2008 |

(Continued)

OTHER PUBLICATIONS

Abarrategui and Krangel (2006) "Regulation of T cell receptor alpha gene recombination by transcription," Nat. Immunol., 7:1109-1115 and Corrigendum.

Allen et al. (1986) "B2-Microglobulin is not required for Cell surface expression of the murine class I histocompatibility antigen H-2Db or of a truncated H-2Db," PNAS, 83:7447-7451.

Altmann et al. (1995) "The T Cell Response to HLA-DR Transgenic Mice to Human Myelin Basic Protein and other Antigens in the Presence and Absence of Human CD4," J. Exp. Med., 181:867-875.

(Continued)

*Primary Examiner* — Thaian N. Ton
*Assistant Examiner* — David A. Montanari
(74) *Attorney, Agent, or Firm* — FisherBroyles, LLP; Rita S. Wu; Margarita Zippin

(57) ABSTRACT

The invention provides genetically modified non-human animals that express chimeric human/non-human MHC I and MHC II polypeptides and/or human or humanized β2 microglobulin polypeptide, as well as embryos, cells, and tissues comprising the same. Also provided are constructs for making said genetically modified animals and methods of making the same. Methods of using the genetically modified animals to study various aspects of human immune system are provided.

21 Claims, 12 Drawing Sheets

Specification includes a Sequence Listing.

(56) References Cited

U.S. PATENT DOCUMENTS

| | | |
|---|---|---|
| 2005/0114910 A1 | 5/2005 | Lone et al. |
| 2006/0107339 A1 | 5/2006 | Gotch et al. |
| 2007/0209083 A1 | 9/2007 | Thiam et al. |
| 2008/0181899 A1 | 7/2008 | Papadopoulos et al. |
| 2008/0219947 A1 | 9/2008 | Linette et al. |
| 2009/0328240 A1 | 12/2009 | Sing et al. |
| 2010/0011450 A1 | 1/2010 | Garcia et al. |
| 2010/0111993 A1 | 5/2010 | Tureci et al. |
| 2010/0138938 A1 | 6/2010 | Garcia et al. |
| 2011/0067121 A1 | 3/2011 | Lone et al. |
| 2013/0111617 A1 | 5/2013 | Macdonald et al. |
| 2013/0117873 A1 | 5/2013 | Wang et al. |
| 2013/0185819 A1 | 7/2013 | Macdonald et al. |
| 2014/0134662 A1 | 5/2014 | Flavell et al. |
| 2014/0245466 A1 | 8/2014 | Macdonald et al. |
| 2015/0040253 A1 | 2/2015 | Macdonald et al. |
| 2015/0245598 A1 | 9/2015 | Macdonald et al. |
| 2015/0342163 A1 | 12/2015 | Voronina et al. |
| 2017/0142944 A1 | 5/2017 | Macdonald et al. |
| 2017/0164590 A1 | 6/2017 | Macdonald et al. |
| 2017/0273286 A1 | 9/2017 | Macdonald et al. |
| 2018/0139940 A1 | 5/2018 | Macdonald et al. |
| 2018/0288986 A1 | 10/2018 | Macdonald et al. |

FOREIGN PATENT DOCUMENTS

| | | |
|---|---|---|
| EP | 1878798 A1 | 1/2008 |
| EP | 0950707 B1 | 2/2009 |
| EP | 1017721 B1 | 2/2009 |
| EP | 1409646 B1 | 6/2012 |
| WO | 199101140 A1 | 2/1991 |
| WO | 199211753 A1 | 7/1992 |
| WO | 199305817 A1 | 4/1993 |
| WO | 199503331 A1 | 2/1995 |
| WO | 1997032603 A1 | 9/1997 |
| WO | 1998024893 A2 | 6/1998 |
| WO | 2001027291 A1 | 4/2001 |
| WO | 2002059263 A2 | 8/2002 |
| WO | 2003006639 A1 | 1/2003 |
| WO | 2005004592 A2 | 1/2005 |
| WO | 2008010099 A2 | 1/2008 |
| WO | 2008010100 A2 | 1/2008 |
| WO | 2009114400 A1 | 9/2009 |
| WO | 2011004192 A1 | 1/2011 |
| WO | 2012007951 A1 | 1/2012 |
| WO | 2012039779 A1 | 3/2012 |
| WO | 2013063340 A1 | 5/2013 |
| WO | 2013063346 A1 | 5/2013 |
| WO | 2014130671 A1 | 8/2014 |
| WO | 2014164638 A1 | 10/2014 |
| WO | 2014164640 A1 | 10/2014 |
| WO | 2016164492 A2 | 10/2016 |

OTHER PUBLICATIONS

Alvarez et al. (1995) "V(D)J Recomination and Allelic Exclusion of a TCR B-Chain Minilocus Occurs in the Absence of a Functional Promoter," J. Immunol., 155:1191-1202.

Arnold and Hammerling (1991) "MHC Class-1 Transgenic Mice," Annu. Rev. Immunol., 9:297-322.

Auerbach et al. (2000) "Establishment and Chimera Analysis of 129/SvEV- and C57BL/6-Derived Mouse Embryonic Stem Cell Lines," BioTechniques, 29:1024-1032.

Baker et al. (1996) "Adaptation of TCR Expression Vectors for the Construction of Mouse-Human Chimeric MBP-Specific TCR Transgenes," J. Neurosci. Research, 45:487-491.

Barber and Lechler (1991) "Interactions between the amino-terminal domains of MCH class II molecules have a profound effect on serologic and T cell recognition: an analysis using recombinant HLA-DR/H-2E molecules," J. Immunol., 147:2346-2353.

Barthold (2004) "Genetically altered mice: phenotypes, no phenotypes, and Faux phenotypes," Genetica, 122:75-88.

Basha et al.(2008) "MHC Class I Endosomal and Lysosomal Trafficking Coincides with Exogenous Antigen Loading in Dendritic cells," PLoS ONE, 3:e3247, 11 pages.

Bassing et al. (2000) Recombination signal sequences restrict chromosomal V(D)J recombination beyond the 12/23 rule, Nature, 405:583-586.

Benmohamed et al. (2000) "Induction of CTL Response by a Minimal Epitope Vaccine in HLA-A*0201/DR1 Transgenic Mice: Dependence on HLA Class II Restricted TH Response," Hum. Immunol., 61:764-779.

Bernabeu et al. (1984) "B2-Microglobulin from serum associates with MHC class I antigens on the surface of cultured cells," Nature, 308:642-645.

Beta-2 microglobulin https://en.wikipedia.org/w/index.php?title=Beta-2_microglobulin&oldid=452509865.

Betser-Cohen et al. (2010) "The Association of MHC Class I Proteins with the 2B4 Receptor Inhibits Self-Killing of Human NK cells," J. Immunol., 184:2761-2768.

Bouffard et al. (1997) "A Physical Map of Human Chromosome 7: An Integrated YAC Contig Map with Average STS Spacing of 79 kb," Genome Research, 7:673-692.

Boyd and Wood (2009) "Variation in MHC expression between undifferentiated mouse ES cells and ES cell derived insulin-producing cell clusters," Transplantation, 87(9):13001304.

Brevini et al. (2010) "Embryonic Stem Cells in Domestic Animals; No shortcuts to pig embryonic stem cells," Theriogenology, 74:544-550.

Buta et al. (2013) "Reconsidering pluripotency tests: Do we still need teratoma assays?," Stem Cell Res., 11:552-562.

Carstea et al. (2009) "Germline competence of mouse ES and iPS Cell lines: Chimera technologies and genetic background," World Journals of Stem Cells, 1(1):22-29.

Chamberlain et al. (1988) "Tissue-specific and Cell surface expression of human major histocompatibility complex class I heavy (HLA-B7) and light (B2-microglobulin) chain genes in transgenic mice," PNAS, 86:7690-7694.

Chung et al. (1994) "Functional three-domain single-chain T-Cell receptors," PNAS, 91:12654-12658.

Clark et al. (1987) "Peptide and nucleotide sequences of rat CD4 (W3/25) antigen: evidence for derivation from a structure with four immunoglobulin-related domains," PNAS, 84(6):1649-1653.

Connolly et al. (1988) "The Lyt-2 Molecule Recognizes Residues in the Class I alpha3 Domain in Allogeneic Cytotoxic T Cell Responses," J. Exp. Med., 168:325-341.

Copper et al. (2007) "An Impaired Breeding Phenotype in Mie with a Genetic Deletion of Beta-2 Microglobulin and Diminished MHC Class I Expression: Role in Reproductive Fitness," Biol. Reprod., 77:274-279.

Corbeil et al. (1996) "HIV-induced Apoptosis Requires the CD4 Receptor Cytoplasmic Tail and Is Accelerated by Interaction of CD4 with p56lck," J. Exp. Med.,183:39-48.

Cosson and Bonifacino (1992) "Role of Transmembrane Domain Interactions in the Assembly of Class II MHC Molecules," Science, 258:659-662.

Crusio et al. (2004) "Flanking Gene and Genetic Background Problems in Genetically Manipulated Mice," Biol. Psychiatry, 56:381-385.

Danner et al. (2011) "Expression of HLA Class II Molecules in Humanized NOD.Rag1KO.IL2RgKO Mice is Critical for Development and Function of Human T and B cells," PLoS ONE, 6:e19826, 12 pages.

Database entry for NCBI Reference Sequence: NG 001333.2 (Sep. 19, 2006) "*Homo sapiens* T cell receptor beta locus (TRB) on chromosome 7".

De Bakker et al. (2006) "A high-resolution HLA and SNP haplotype map for disease association studies in the extended human MHC," Nature Genet., Online Supplement, 33 pages.

De Bakker et al. (2006) "A high-resolution HLA and SNP hapotype map for disease association studies in the extended human MHC," Nature Genet., 38:1166-1172.

De Gassart et al. (2008) "MHC class II stabilization at the surface of human dendritic cells is the result of maturation-dependent MARCH I down-regulation," PNAS, 105:3491-3496.

(56) References Cited

OTHER PUBLICATIONS

Dennis (2002) "Welfare issues of genetically modified animals," ILAR Journal, 43(2):100-109.
Doetschman (2009) "Influence of Genetic Background on Genetically Engineered Mouse Penotypes," Methods Mol. Biol., 530:423-433.
Dolan et al. (2004) "Invariant Chain and the MHC Class II Cytoplasmic Domains Regulate Localization of MHC Class II Molecules to Lipid Rafts in Tumor Cell-Based Vaccines," J. Immunol., 172:907-914.
Duke (1989) "Self Recognition by T Cell," J. Exp. Med. 170:59-71.
El Fakhry et al. (2004) "Delineation of the HLA-DR Region and the Residues Involved in the Association with the Cytoskeleton," J. Biol. Chem., 279:18472-18480.
Ellmeier et al. (1998) "Multiple developmental stage-specific enhancers regulate CD8 expression in developing thymocytes and in thymus-independent T cells," Immunity, 9(4):485-496.
Festing et al. (1999) "Revised nomenclature for strain 129 mice," Mamm. Genome, 10:836.
Firat et al. (2002) "Comparative analysis of the CO8+ T Cell repertoires of H-2 class I wild-ype/HLA-2.1 and H-2 class I knockout/HLA-A2.1 transgenic mice," Internal. Immunol., 14:925-934.
Fleischer et al. (1996) Reactivity of Mouse T-Cell Hybridomas Expressing Human Vβ Gene Segments with Staphylococcal and Streptococcal Superantigens, Infection and Immunity, 64(3):997-994.
Fooksman et al. (2009) "Cutting Edge: Phospholidylinositol 4, 5-Bisphosphate Concentration at the APC Side of the Immunological Synapse Is Required for Effector T Cell Function," J. Immunol., 182:5179-5182.
Friese et al., (2008) "Opposing effects of HLA class I molecules in tuning autoreactive CD8+ T cells in multiple scelerosis," Nature Med., 14(11): 1227-1235.
Fugger et al. (1994) "Expression of HLA-DR4 and human CD4 transgenes in mice determines the variable region beta-chain T-Cell repertoire and mediates an HLA-DR-restricted immune response," PNAS, 91:6151-6155.
Fukui et al. (1993) "T-cell repertoire in a stain of transgenic C57BL/6 mice with the HLA-DRA gene on the X-chromosome," Immunogenetics, 37(3):204-211.
Fukui et al. (1997) "Differential requirement of MHC class II molecules expressed on hematopoietic cells for positive selection of CD4+ thymocytes in TCR α β and TCR β transgenic mice," Internal. Immunol., 9(9):1385-1391.
Gao et al. (1997) "Crystal structure of the complex between human CD88alpha-alpha and HLA-A2," Nature, 387:630-634.
Gao et al. (2000) "Molecular interactions of coreceptor CD8 and MHC class 1: the molecular basis for functional coordination with the T-Cell receptor," Immunol. Today, 21 (12):630-636.
Germain et al., (2002) "T-Cell Development and the CD4-CD8 Lineage Decision, Nature Reviews, Immunol.," 2:309-322.
Goldman et al. (2004) "Transgenic animals in medicine: Integration and expression of foreign genes, theoretical and applied aspects," Med. Sci. Monit., 10(11): RA274-285.
Gruda et al. (2007) "Intracellular Cysteine Residues in the Tail of MHC Class I Proteins Are Crucial for Extracellular Recognition by Leukocyte Ig-Like Receptor 1," J. Immunol., 179:3655-3661.
Günther and Walter (2001) "The major histocompatibility complex of the rat (Rattus norvegicus)," Immunogenetics, 53:520-542.
Gur et al. (1997) "Structural Analysis of Class I MHC Molecules: The Cytoplasmic Domain Is Not Required for Cytoskeletal Association, Aggregation and Internalization," Mol. Immunol., 34:125-132.
Güssow et al. (1987) "The Human B2-Microglobulin Gene. Primary Structure and Definition of the Transcriptional Unit," J. Immunol., 139:3132-3138.
Haks et al. (1999) "Cell-fate decisions in early T cell development: regulation by cytokine receptors and the pre-TCR," Immunol., 11:23-37.

Hanna et al. (1994) "Specific expression of the human CD4 gene in mature CD4 + CD8− and immature CD4+ and CD8+ T cells and in macrophages of transgenic mice," Mol. Cellular Biol., 14(2):1084-1094.
Harton et al. (2016) "Immunological Functions of the Membrane Proximal Region of MHC Class II Molecules," F1000Research, 5:1-12, doi: 10.12688/f1000research.7610.1.
Holdsworth et al. (2009) "The HLA dictionary 2008: a summary of HLA-A, -B, -C-DRB1/3/4/5, and -DQB1 alleles and their association with serologically defined HLA-A, -B, -C, -DR, and -DO antigens," Tissue Antigens, 73:95-170.
Hong et al. (2012) "Derivation and Characterization of Embryonic Stem Cells Lines Derived from Transgenic Fischer 344 and Dark Agouti Rats," Stem Cells and Development, 21(9):1571-1586.
Hostert et al. (1997) "A CD8 genomic fragment that directs subset-specific expression of CD8 in transgenic mice," J. Immunol., 158(9):4270-4281.
Houdebine, et al (2002) "The methods to generate transgenic animals and to control transgene expression," J. of Biotech., 98:145-160.
Houdebine, et al (2007) "Methods in Molecular," Biology, 360:163-202.
Huang et al. (1997) "Analysis of the contact sites on the CD4 Molecule with Class II MHC Molecule," J. Immunol., 158:215-225.
International MHC and Autoimmunity Genetics Network (IMAGEN) (2009) "Mapping of multiple 40 susceptibility variants within the MHC region for 7 immune-mediated diseases," PNAS, 1 06: 18680-18685.
Irie et al. (1998) "The cytoplasmic domain of CD8 beta regulates Lck kinase activation and CD8 T cell development," J. Immunol., 161(1):183-191.
Irwin et al. (1989) "Species-restricted interactions between CD8 an the alpha3 domain of class I influence the magnitude of the xenogeneic response," J. Exp. Med., 170:1091-1101.
Ishimoto et al. (1997) "In vitro and in vivo evidence for high frequency of I-Ab-reactive CD4+ t cells in HLA-DQ or HLA-DRA transgenic mice lacking endogenous MHC class I and/or class II expression," J. Immunol., 159(8):3717-3722.
Itano et al. (1996) "The Cytoplasmic Domain of CD4 Promotes the Development of CD4 Lineage T Cells," J. Exp. Med., 183(3):731-741.
Ito et al. (1996) "HLA-DR4-IE Chimeric Class II Transgenic, Murine Class 11-Deficient Mice Are Susceptible to Experimental Allergic Encephalomyelitis," J. Exp. Med., 183:2635-2644.
Jakobovits (1994) "Humanizing the mouse genome," Cur. Biol., 4(8):761-763.
Johansson et al. (2005) "Natural killer Cell education in mice with single or multiple major histocompatibility complex class I molecules," J. Exp. Med., 201:1145-1155.
Josson et al. (2011) "B2 microglobulin induces epithelial to mesenchymal transition and confers cancer lethality and bone metastasis in human cancer cells," Cancer Res., 71:1-11.
Kalinke et al. (1990) "Strong Xenogeneic HLA Response in Transgenic Mice after Introducing an Alpha3 Domain into HLA B27," Nature, 348:642-644.
Kaplan et al. (2005) "A new murine tumor model for studying HLA-A2-restricted anti-tumor immunity," Cancer Letters, 224:153-166.
Khor et al. (2002) "Allelic exclusion at the TCRβ locus," Curr. Opin. Immunol., 14:230-234.
Kievits et al. (1987) "HLA-restricted recognition of viral antigens in HLA transgenic mice," Nature 329:447-449.
Killeen et al. (1993) "Regulated expression of human CD4 rescues helper T cell development In mice lacking expression of endogenous CD4," EMBO J., 12(4): 1547-1553.
Kioussis et al. (2002) "Chromatin and CD4, CD8A and CD8B gene expression during thymic differentiation," Nature Rev. Immunol., 2(12):909-919.
Kirwan et al. (2005) "Killer Cell Ig-Like Receptor-Dependent Signaling by Ig-Like Transcript 2 (ILT2/CD85j/LILRB1/ LIR-1)," J. Immunol., 175:5006-5015.

(56) References Cited

OTHER PUBLICATIONS

Koller and Orr (1985) "Cloning and complete sequence of an HLA-A2 gene: Analysis of two HLA-A Alleles at the nucleotide Level" J. Immunol. 134(4):2727-2733.
Koller et al. (1990) "Normal Development of Mice Deficient in B2M, MHC Class I Proteins, and CD8+ T cells," Science, 248:1227-1230.
Koop et al., (1994) "The human T-cell receptor TCRAC/TCRDC (C alpha/C delta) region: organization, sequence, and evolution of 97.6 kb of DNA," Genomics 19(3):478-493.
Krangel et al. (1998) "Development regulation of V(D)J recombination at the TCR α/δ locus," Immunol. Rev., 165:131-147.
Kruisbeek et al., (2000) "Branching out to gain control: how the pre-TCR is linked to multiple functions," Rev. Immunol. Today, 21 (12):637-644.
Kumanovics et al. (2003) "Genomic Organization of the Mammalian MHC," Annu. Rev. Immunol., 21:629-657.
Laface et al. (1995) "Human CD8 Transgene Regulation of HLA Recognition by Murine T cells," J. Exp. Med., 182:1315-1325.
Landau et al. (1988) "The envelope glycoprotein of the human immunodeficiency virus binds to the immunoQiobulin-like domain of CD4," Nature, 334(6178): 159-162.
Laub et al. (2000) "A multiple transgenic mouse model with a partially humanized activation pathway for helper T cell responses," J. Immunol. Methods, 246(1-2):37-50.
Lauzurica P. and Krangel M.S. (1994) "Enhancer-dependent and -independent Steps in the Rearrangement of a Human T Cell Receptor Delta Transgene," J. Exp. Med., 179:43-55.
Lavial and Pain (2010) "Chicken embryonic stem cells as a non-mammalian embryonic stem cell model," Develop. Growth Differ., 52:101-114.
Law et al. (1994) "Human CD4 Restores Normal T Cell Development and Function in Mice Deficient in Murine CD4," J. Exp. Med., 179(4): 1233-1242.
Leahy (1995) "A structural view of CD4 and CD8," FASEB J., 9:17-25.
Leduc et al. (2000) "T Cell Development in TCRβ Enhancer-Deleted Mice: Implications for αβ T Cell Lineage Commitment and Differentiation," J. Immunol., 165:1364-1373.
Lee et al. (1982) "Sequence of an HLA-DR alpha-chain eDNA clone and intron-exon organization of the corresponding gene," Nature, 299:750-752.
Li et al. (2009) "Mamu-A*01/Kb transgenic and MHC Class I knockout mice as a tool for HIV vaccine development," Virology, 387:16-28.
Li et al. (2010) "Transgenic mice with a diverse human T Cell antigen receptor repertoire," Nature Med., 16(9):1029-1034, doi:10.1038/nm.2197.
Li et al. (2013) "Generation of transgenic mice with megabase-sized human yeast artificial chromosomes by yeast spheroplast-embryonic stem cell fusion," Nat. Protoc., 8(8):1567-1582, doi:10.1038/nprot.2013.093.
Li et al. (2016) "The Implication and Significance of Beta 2 Microglobulin: A Conservative Multifunctional Regulator," Chinese Medical Journal, 129(4):448-455.
Lie and Petropoulos (1998) "Advances in quantitative PCR technology: 5' nuclease assays," Curr. Opin. Biotech., 9:43-48.
Linnenbach et al. (1980) "DNA-transformed murine teratocarcinoma cells: regulation of expression of simian virus 40 tumor antigen in stem versus differentiated cells," PNAS, 77(8):4875-4879.
Littman (1987) "The Structure of the CD4 and CD8 Genes," Annual Review of Immunology, 5:561-584.
Lizee et al. (2003) "Control of dendritic cell cross-presentation by the major histocompatibility complex class I cytoplasmic domain," Nature Immunol., 4:1065-1073.
Lynch et al. (2009) "Novel MHC Class I Structures on Exosomes," J. Immunol., 183:1884-1891.
Maddon et al. (1987) "Structure and expression of the human and mouse T4 genes," PNAS, 84(24):9155-9159.

Madsen et al. (1999) "A humanized model for multiple sclerosis using HLA-DR2 and a human T-cell receptor," Nature Genet., 23:343-347.
Magliocca et al. (2006) "Undifferentiated Murine Embryonic Stem Cells Cannot Induce Portal Tolerance but May Possess Immune Privilege Secondary to Reduced Major Histocompatibility Complex Antigen Expression," Stem Cells and Development, 15(5):707-717.
Maksimenko et al. (2013) "Use of Transgenic Animals in Biotechnology: Prospects and Problems," ACTNA Naturae, 5(1):33-46.
Manz et al. (2009) "Renaissance for mouse models of human hematopoiesis and immunobiology," Nature Immunology, 10(10):1039-1042.
Marsh et al. (2010) "Nomenclature for factors of the HLA system," 2010, Tissue Antigens, 75:291-455.
Marten et al. (2003) "Transgenic mouse methods and protocols," Methods in Molecular Biology, 209:51-58.
Mendez et al. (1997) "Functional transplant of megabase human immunoglobulin loci recapitulates human antibody response in mice," Nature Genet., 15(2):146-156.
Miao (2012) "Recent Advances and Applications of Transgenic Animal Technology," Polymerase Chain Reaction, Dr. Patricia Hernandez-Rodriguez (Ed.), ISBN: 978-953-51-0612-8, InTech, pp. 255-282, Available from: http://www.intechopen.com/books/polymerase-chain-reaction/recent-advances-and-applications-of-transgenic-animal-technology.
Moir et al. (1996) "Postbinding events mediated by human immunodeficiency virus type 1 are sensitive to modifications in the D4-transmembrane linker region of CD4," J. Virology, 70(11):8019-8028.
Moldovan et al. (2002) "CD4 Dimers Constitute the Functional Component Required forT Cell Activation," J. Immunol., 169:6261-6268.
Mombaerts P. et al. (1991) "Creation of a large genomic deletion at the T-cell antigen receptor β-subunit locus in mouse embryonic stem cells by gene targeting," PNAS, 88:3084-3087.
Mombaerts et al. (1992) "Mutations in T-cell antigen receptor genes a and B block thymocyte development at different stages," Nature, 360:225-231.
Mombaerts et al. (1993) "Spontaneous Development of Inflammatory Bowel Disease in T Cell Receptor Mutant Mice," Cell, 75:275-282.
Munoz et al. (2008) "Technical note; Conventional pluripotency markers are unspecific for bovine embryonic-derived cell-lines," Theriogenology, 69:1159-1164.
Murphy et al. (2008) "Janeway's Immunobiology" 7th ed., Garland Science, pp. 125-13B and 196-213.
Musser G. (Encyclopedia Britannica, May 31, 2016) Rodent, Mammal, http://www.britannica.com/animal/rodent.
Nakayama et al. (1992) "Recent Duplication of the Two Human CD8 β-chain genes," J. Immunol., 148:1919-1927.
Nickerson et al. (1990) "Expression of HLA-B27 in Transgenic Mice Is Dependent on the Mouse H-20 Genes," J. Exp. Med., 172:1255-1261.
Noordzij et al. (2000) "N-terminal truncated human RAG1 proteins can direct T-cell receptor but not immunogiobulin gene rearrangements," Blood, 96(1):203-209.
Norment et al. (1988) "A second subunit of CD8 is expressed in human T cells," EMBO J., 7(11):3433-3439.
Norment et al. (1989) "Alternatively Spliced mRNA Encodes a Secreted Form of Human CD8α, Characterization of the Human CD8α gene," J. Immunol. 142:3312-3319.
Ostrand-Rosenberg et al. (1991) "Abrogation of Tumorigenicity by MHC Class II Antigen Expression Requires the Cytoplasmic Domain of the Class II Molecule," J. Immunol., 147:2419-2422.
Pajot et al. (2004) "A mouse model of human adaptive immune functions: HLA-A2.1/HLA-DR1-trasngenic H-2 class 1-/class 11-knock-out mice," Eur. J. Immunol., 34:3060-3069.
Paris and Stout (2010) "Embryonic Stem Cells in Domestic Animals; Equine embryos and ebryonic stem cells: Defining reliable markers of pluripotency," Theriogenology, 74:516-524.
Parnes, et al. (1982) "Structure of Wild-Type and Mutant Mouse $β_2$-Microglobulin Genes," Cell, 29:661-669.

(56) References Cited

OTHER PUBLICATIONS

Pasare et al. (2001) "T cells in mice expressing a transgenic human TCRβ chain get positively selected but cannot be activated in the periphery by signaling through TCR," Intl. Immunol., 13(1):53-62.
Pascolo, et al. (1997) "HLA-A2.1-restricted Education and Cytolytic Activity of CD8+ T Lymphocytes from from β2 Microglobulin (β2m) HLA-A2.1 Monochain Transgenic H-2Db β2m Double Knock-out Mice," J. Exp. Med., 185:2043-2051.
Pascolo, et al. (2005) "HLA class I transgenic mice: development, utilisation and improvement," Expert Opinion Biol. Ther., 5(7):919-938.
Perarnau et al. (1988) "Human B2-microglobulin specifically enhances cell-surface expression of HLA class I molecules in transfected murine cells," J. Immunol., 141:1383-1389.
Petitte et al. (2004) "Avian pluripotent stem cells," Mechanisms of Development, 121:1159-1168.
Pettersen et al. (1998) "The TCR-Binding Region of the HLA Class I α2 Domain Signals Rapid Fast Independent Cell, Death: A Direct Pathway for T Cell-Mediated Killing of Target cells," J. Immunol., 160:4343-4352.
Pittet et al. (2003) "Alpha3 Domain Mutants of Peptide/MHC Class I Multimers Allow the Selective Isolation of High Avidity Tumor-Reactive CD8 T cells," J. Immunol., 171:1844-1849.
Potter et al. (1989) "Substitution at residue 227 of H-2 class I molecules abrogates recognition by CD8-dependent, but not CD8-independent, cytotoxic T lymphocytes," Nature, 337:73-75.
Poueymirou et al. (2007) "F0 generation mice fully derived from gene-targeted embryonic stem cells allowing immediate phenotypic analyses," Nature Biotech., 25:91-99.
Quinn et al. (1997) "Virus-Specific, CD8+ Major Histocompatibility Complex Class 1-Restricted Cytotoxic T Lymphocytes in Lymphocytic Choriomeningitis Virus-Infected B2-Microglobulin-Deficient Mice," J. Virol., 71:8392-8396.
Rack et al. (1997) "A Chromosome 14q11/TCRα/δ Specific Yeast Artificial Chromosome Improves the Detection Rate and Characterization of Chromosome Abnormalities in T-Lymphoproliferative Disorders," Blood, 90(3):1233-1240.
Raffegerst et al. (2009) "Diverse Hematological Malignancies Including Hodgkin-Like Lymphomas Develop in Chimeric MHC Class II Transgenic Mice," PLoS ONE, 4:e8539, 12 pages.
Reipert et al. (2009) "Opportunities and limitations of mouse models humanized for HLA class II antigens," Thrombosis and Haemostasis, 7(Suppl. 1):92-97.
Ren et al. (2006) "Construction of bioactive chimeric MHC class I tetramer by expression and purification of human-murine chimeric MHC heavy chain and β2M as a fusion protein in *Escherichia coli*," Protein Expression and Purification, 50:171-78.
Rodriguez-Cruz et al. (2011) "Natural Splice Variant of MHC Class I Cytoplasmic Tail Enhances Dendritic Cell-Induced CD8+ T-Cell, Responses and Boosts Anti-Tumor Immunity," PLoS ONE, 6:e22939, 10 pages.
Rohrlich et al. (2003) "HLA-B*0702 transgenic, H-2K$^b$D$^b$ doubleknockout mice: phenotypical and functional characterization in response to influenza virus," International Immunology, 15(6):765-772.
Rosano et al. (2005) "The three-dimensional structure of B2 microglobulin: Results from X-ray crystallography," Biochim. Biophys. Acta, 1753:85-91.
Rothe et al. (1993) Functional expression of a human TCRβ gene in transgenic mice, Intl. Immunol., 5(1):11-17.
Rowen et al., (1996) "The Complete 685-Kilobase DNA Sequence of the Human β T Cell Receptor Locus," Science, 272:1755-1762.
Rubio et al. (2004) "Cross-linking of MHC class I molecules on human NK cells inhibits NK cell function, segregates MHC I from the NK cell synapse, and induces intracellular phosphotyrosines," J. Leukoc. Biol., 76:116-124.
Salter et al. (1989) "Polymorphism in the alpha3 domain of HLA-A molecules affects binding to CD8," Nature, 338:345-347.
Salter et al. (1990) "A binding site for the T-cell co-receptor CD8 on the alpha 3 domain of HLA-A2," Nature, 345:41-46.
Samberg et al. (1989) "The α3 domain of major histocompatibility complex class I molecules plays a critical role in cytotoxic T lymphocyte stimulation," Eur. J. Immunol., 19(12):2349-2354.
Sanders et al. (1991) "Mutations in CD8 that Affect Interactions with HLA Class I and Monoclonal Anti-CD8 Antibodies," J. Exp. Med., 174:371-379.
Santagata et al. (2000) "The genetic and biochemical basis of Omenn syndrome," Immunological Reviews, 178:64-74.
Scheer et al. (2013) "Generation and utility of genetically humanized mouse models." Drug Discovery Today, 18(23/24):1200-1211.
Schwarz et al. (1996) "RAG mutations in human B cell negative SCID," Science, 274(5284):97-99.
Sebzda et al. (1999) "Selection of the T Cell Repertoire," Annu. Rev. Immunol., 17:829-874.
Shankar Pradhan and Majumdar, (2016) "An Efficient Method for Generation of Transgenic Rats Avoiding Embryo Manipulation," Molecular Therapy—Nucleic Acids, 5, e293:1-11 doi:10.1038/mtna.2016.9.
Shankarkumar (2004) "The Human Leukocyte Antigen (HLA) System," Int. J. Hum. Genet., 4:91-103.
Sherman et al. (1992) "Selecting T Cell Receptors with High Affinity for Self-MHC by Decreasing the Contribution of CD8," Science, 258:815-818.
Shields et al. (1998) "Functional comparison of bovine, murine, and human β$_2$-microglobulin: interactions with murine MHC I molecules," Molecular Immunology, 35:919-928.
Shin et al. (2006) "Surface expression of MHC class II in dendritic cells is controlled by regulated ubiquitination," Nature, 444:115-118.
Shinkai et al. (1992) "RAG-2-deficient mice lack mature lymphocytes owing to inability to initiate V(D)J rearrangement," Cell 68(5):855-67.
Shinohara et al. (2007) "Active integration: new strategies for transgenesis," Transgenic Res., 16:333-339.
Shiroishi et al. (2003) "Human inhibitory receptors Ig-like transcript 2 (ILT2) and ILT4 compete with CD8 for MHC class I binding and bind preferentially to HLA-G," PNAS, 100:8856-8861.
Shultz et al. (2007) "Humanized mice in translational biomedical research," Nature Rev., 7:118-130.
Sigmund (2000) "Viewpoint: Are Studies in Genetically Altered Mice Out of Control?," Arterioscler. Thromb. Vasc. Biol., p. 1425-1429.
Sims et al (2004) "Genetic Susceptibility to Ankylosing Spondylitis," Cur. Mol. Med., 4(1):13-20.
Singer et al. (2008) "Lineage fate and intense debate: myths, models and mechanisms of CD4/CDS lineage choice," Nature Rev. Immunol., 8(10):788-801.
Siu et al. (1994) "A transcriptional silencer controls the developmental expression of the CD4 gene," EMBO J., 13(15):3570-3579.
Sleckman et al. (2000) "Mechanisms that direct ordered assembly of T cell receptor β locus V, D, and J gene segments," PNAS, 97(14):7975-7980.
Smiley et al. (1995) "Transgenic mice expressing MHC class II molecules with truncated A-beta cytoplasmic domains reveal signaling-independent defects in antigen presentation," Internal. Immunol., 7:665-677.
Smiley et al. (1996) "Truncation of the class II beta-chain cytoplamic domain influences the level of class II/invariant chain-derived peptide complexes," PNAS, 93:241-244.
Street et al. (2002) "Limitations of HLA-transgenic mice in presentation of HLA-restricted cytotoxic T-cell epitopes from endogenously processed human papillomavirus type 16 E7 protein," Immunology, 106:526-536.
Takaki et al. (2006) "HLA-A*0201-Restricled T cells from Humanized NOD Mice Recognize Autoantigens of Potential Clinical Relevance to Type I Diabetes," J. Immunol., 176:3257-3265.
Tanabe et al. (1989) "Analysis of xenoantigenicity of HLA Class I molecules by a complete series of human-mouse hybrid genes," Transplantation, 48:1, 135-140.
Taneja and David (1998) "HLA Transgenic Mice as Humanized Mouse Models of Disease and Immunity," J. Clin. Invest., 101:921-926.

(56) References Cited

OTHER PUBLICATIONS

Taneja and David (2009) "Spontaneous autoimmune myocarditis and cardiomyopathy in HLA-DQ8.NODAbo transgenic mice," Journal of Autoimmunity 33:260-269.
Taylor et al. (1993) "Human immunoglobulin transgenes undergo rearrangement, somatic mutation and class switching in mice that lack endogenous IgM," Int. Immunol., 6(4):579-591.
Theobald et al. (1995) "Targeting p53 as a general tumor antigen," PNAS, 92:11993-11997.
Tishon et al. (2000) "Transgenic Mice Expressing Human HLA and CD8 Molecules Generate HLA-Restricted Measles Virus Cytotoxic T Lymphocytes of the Same Specificity as Humans with Natural Measles Infection," Virology, 275:286-293.
Tong et al. (2010) "Production of p53 gene knockout rats by homologous recombination in embryonic stem cells," Nature Letters, 467:211-215.
Toyonaga et al. (1985) "Organization and sequences of the diversity, joining, and constant region genes of the human T-cell receptor beta chain," PNAS. 82(24):8624-8628.
Ureta-Vidal et al. (1999) "Phenotypical and Functional Characterization of the CD8 + T Cell Repertoire of HLA-A2.1 Transgenic, H-2Kb°Db° Double Knockout Mice," J. Immunol., 163:2555-2560.
Valenzuela et al. (2003) "High-throughput engineering of the mouse genome coupled with high-resolution expression analysis", Nature Biotech., 21:652-659.
Vignali et al. (1992) "Species-specific Binding of CD4 to the Beta2 Domain of Major Histocompatibility Complex Class II Molecules," J. Exp. Med., 175:925-932.
Vignali et al. (1996) "The Two Membrane Proximal Domains of CD4 Interact with the T Cell Receptor," J. Exp. Med., 183:2097-2107.
Villa et al. (1998) "Partial V(D)J recombination activity leads to Omenn syndrome," Cell 93(5): 855-896.
Villa et al. (1999) "Omenn syndrome: a disorder of Ragl and Rag2 genes," J. Clin. Immunol., 19(2):87-97.
Viney et al. (1992) "Generation of Monoclonal Antibodies Against a Human T Cell Receptor β chain Expressed in Transgenic Mice," Hybridoma, 11(6):701-714.
Vitiello et al. (1991) "Analysis of the HLA-restricted Influenza-specific Cytotoxic T Lymphocyte Response in 6 Transgenic Mice Carrying a Chimeric Human-Mouse Class I Major Histocompatibility Complex," J. Exp. Med., 173:1007-1015.
Vollmer et al. (2000) "Antigen contacts by Ni-reactive TCR: typical αβ chain cooperation versus a chain-dominated specificity," IntL. Immunol.,12(12):1723-1731.
Vugmeyster et al. (1998) "Major histocompatibility complex (MHC) class I KbDb -/- deficient mice possess functional CD8 + T cells and natural killer cells," PNAS, 95:12492-12497.
Wagner et al. (1994) "Antibodies generated from human immunoglobulin miniloci in transgenic mice," Nucleic Acids Res., 22(8):1389-1393.
Wagner et al. (1994) "Ligation of MHC Class I and Class II Molecules Can Lead to Heterologous Desensitization of Signal Transduction Pathways That Regulate Homotypic Adhesion in Human Lymphocytes," J. Immunol., 152:5275-5287.
Wagner et al. (1994) "The diversity of antigen-specific monoclonal antibodies from transgenic mice bearing human immunogiobulin gene miniloci," Eur. J. Immunol., 24(11):2672-2681.
Wang and Reinherz (2001) "Structural basis of T cell recognition of peptides bound to MHC molecules," Mol. Immunol., 38:1039-1049.
Wei et al. (1996) "Repertoire and Organization of Human T-Cell Receptor α Region Variable Genes," Short Communication, Genomics, 38:442-445.
Wen et al. (1998) "Induction of Insulitis by Glutamic Acid Decarboxylase Peptide-specific and HLA-DQ8-restricted CD4+ T Cells from Human DQ Transgenic Mice," J. Clin. Invest., 102(5):947-957.
Willcox et al. (2003) "Crystal structure of HLA-A2 bound to LIR-1, a host and viral major histocompatibility complex receptor," Nature Immunol., 4:913-919.

Wong and Wen (2004) "What can the HLA transgenic mouse tell us about autoimmune diabetes?," Diabetologia, 47:1476-1487.
Woodle et al. (1997) "Anti-Human Class I MHC Antibodies Induce Apoptosis by a Pathway That Is Distinct from the Fas Antigen-Meidaled Pathway," J. Immunol., 158:2156-2164.
Woods et al. (1994) "Human Major Histocompatibility Complex Class 11-Restricted T Cell, Responses in Transgenic Mice," J. Exp. Med., 180:173-181.
Wooldridge et al. (2010) "MHC Class I Molecules with Superenhanced CD8 Binding Properties Bypass the Requirement for Cognate TCR Recognition and Nonspecifically Activate CTLs," J. Immunol., 184:3357-3366.
Wu et al. (1997) "Dimeric association and segmental variability in the structure of human CD4," Nature, 387:527.
Yamamoto et al. (1994) "Functional Interaction between Human Histocompatibility Leukocyte Antigen (HLA) Class 27 II and Mouse CD4 Molecule in Antigen Recognition by T cells in HLA-DR and DQ Transgenic Mice," J. Exp. Med., 180:165-171.
Yoshikai et al. (1985) "Organization and sequences of the variable, joining and constant region genes of the human T-cell receptor alpha-chain," Nature, 316(6031):837-840.
Zamoyska (1998) "CD4 and CDS: modulators of T cell receptor recognition of antigen and of immune responses?," Curr. Opin. Immunol., 10:82-87.
Zhou et al., (2009) "Developing tTA transgenic rats for inducible and reversible gene expression," International Journal of Biological Sciences, 5:171-181.
Zijlstra et al. (1990) "B2-Microglobulin deficient mice lack CD4-8+ cytolytic T Cells," Nature, 344:742-746.
Zumla et al. (1992) "Co-expression of human T cell receptor chains with mouse CD3 on the cell surface of a mouse T cell hybridoma," J. Immunol. Methods., 149(1):69-76.
Zumla et al. (1992) "Use of a murine T-cell hybridoma expressing human T-cell receptor alpha- and betagene products as a tool for the production of human T-cell receptor-specific monoclonal antibodies," Human Immunol., 35(3):141-148.
International Search Report and Written Opinion for PCT/US2014/023076, dated Jul. 18, 2014.
International Search Report and Written Opinion for PCT/US2012/062042, dated Feb. 18, 2013.
International Search Report and Written Opinion for PCT/US2012/062029, dated Feb. 28, 2013.
International Search Report and Written Opinion for PCT/US2014/023068, dated Jul. 24, 2014.
International Search Report and Written Opinion for PCT/US2014/017395, dated Jun. 2, 2014.
International Search Report and Written Opinion for PCT/US2014/017387, dated Jun. 2, 2014.
International Search Report and Written Opinion for PCT/US2016/026260, dated Aug. 11, 2016.
Extended European Search Report with respect to Europe Application No. 17184955.7, dated Nov. 24, 2017.
English Translation of Office Action with Respect to Japan Application No. 2014-539027 dated Sep. 6, 2016.
Statement of Relatedness under MPEP 2001.06 with Respect to U.S. Appl. No. 16/184,473 dated Sep. 19, 2019.
Cheuk et al. "Human MHC Class I Transgenic Mice Deficient for H2 Class I Expression Facilitate Identification and Characterization of New HLA Class I-Restricted Viral T Cell Epitopes," Journal of Immunology, 2002, 169:5571-5580.
Epstein et al. "Expression and function of HLA-A2.1 in transgenic mice," Eur. J. Immunol., 1989, 19:1575-1583.
Newberg et al. "Importance of MHC class I alpha2 and alpha3 domains in the recognition of self and non-self MHC molecules," Journal of Immunology, 1996, 156:2473-2480.
Statement of Relatedness under MPEP 2001.06 with Respect to U.S. Appl. No. 16/184,473 dated Oct. 8, 2019.
Anderson (2008) "Post-transcriptional control of cytokine production," Nature Immunology, 9(4):353-359.
Bonnet, et al. (2009) "Molecular Genetics at the T-Cell Receptor β Locus: Insights into the Regulation of V(D)J Recombination," V(D)J Recombination, 650:116-132.

(56) References Cited

OTHER PUBLICATIONS

Cameron, E. (1997) "Recent Advances in Transgenic Technology," Molecular Biotechnology, 7:253-265.
Carpenter, et al. (2014) "Post-transcriptional regulation of gene expression in innate immunity," Nature Reviews Immunology, 14:361-376.
Giraldo and Montoliu (2001) "Size matters: use of YACs, BACs and PACs in transgenic animals," Transgenic Research, 10:83-103.
Houdebine, (1994) "Production of pharmaceutical proteins from transgenic animals," J. Biotechnology, 34:269-287.
Kappel et al. (1992) "Regulating gene expression in transgenic animals," Current Opinion in Biotechnology, 3:548-553.
Nowak et al. (1992) "The optimal number of major histocompatibility complex molecules in an individual," Immunology, 89:10896-10899.
Rock et al. (2016) "Present Yourself! by MHC Class I and MHC Class II Molecules," Trends Immunol., 37(11):724-737.
Scardino et al. (2003) "In vivo study of the GC90/IRIV vaccine for immune response and autoimmunity into a novel humanised transgenic mouse," British Journal of Cancer, 89:199-205.
Sundelin et al. (1988) "The Complete Amnio Acid Sequence of Rat β2-Microglobulin," Scand. J. Immunol., 27:195-199.
Tran et al. (2006) "Additional human β2-microglobulin curbs HLA-B27 misfolding and promotes arthritis and spondylitis without colitis in male HLA-B27-transgenic rats," Arthritis & Rheumatism, 54:1317-1327.
Willinger et al. (2011) "Improving human hemato-lymphoid-system mice by cytokine knock-in gene replacement," Trands in Immunology, 32(7):321-327.
Statement of Relatedness under MPEP 2001.06 with Respect to U.S. Appl. No. 16/184,473 dated Jun. 16, 2020.
Brouwers et al. (2015) "Unexpected Phenotypes in Mouse Models Carrying the Human Growth Hormone Minigene to Enhance Transgene Expression," Journal of Steroids & Hormonal Science, 6(2):1000.ell5 (2 pages).
Cao et al., (2009) "Isolation and Culture of Primary Bovine Embryonic Stem Cell Colonies by a Novel Method," Journal of Experimental Zoology, 311A:368-376.
Choi et al., (2011) "Expression of the metabotropic glutamate receptor 5 (mGluR5) induces melanoma in transgenic mice," PNAS, 108(37):1519-15224.
Glick and Pasternak Dzh. Moleculyarnaya biotehnologiya. Printsipy i primeneniye. Moscow: Mir, 2002 (with English translation).
Gomez et al. (2010) "Derivation of cat embryonic stem-like cells from in vitro-produced blastocysts on homologous and heterologous feeder cells," Theriogenology, 74:498-515.
HALL (2008) "Porcine Embryonic Stem Cells: A Possible Source for Cell Replacement Therapy," Stem Cell Rev., 4:275-282.
Hou et al. (2016) "Derivation of Porcine Embryonic Stem-Like Cells from In Vitro-Produced Blastocyst-Stage Embryos," Scientific Research, 6:1-13.
Houdebine (2009) Methods to Generate Transgenic Animals, Genetic Engineering in Livestock, New Applications and Interdisciplinary Perspectives, Engelhard M, et al., 2009, XVI, 1 46 p. 8 illus., pp. 31-47, see p. 36.
Intarapat and Stern (2013) "Chick stem cells: Current progress and future prospects," Stem Cell Res., 11:1378-1392.
Jean et al. (2013) "Pluripotent genes in avian stem cells," Develop. Growth Differ., 55:41-51.
Kawamata and Ochiya (2010) "Generation of genetically modified rats from embryonic stem cells," PNAS, 107(32):14223-14228.
Lavial et al., (2008) "Molecular control of pluripotency and germ line competency in chicken embryonic stem cells," Cell Research, 18:s106 (1 page).
Murphy and Silha (2000) "Unexpected and unexplained phenotypes in transgenic models," Growth Hormone & IGF Research, 10:233-235.
Yantha et al., (2010) "Unexpected Acceleration of Type 1 Diabetes by Transgenic Expression of B7-H1 in NOD Mouse Peri-Islet Glia," Diabetes, 59:2588-2596.
Statement of Relatedness under MPEP 2001.06 with Respect to U.S. Appl. No. 16/184,473 dated Apr. 7, 2021.
Linder C. (2006) "Genetic Variables That Influence Phenotype," ILAR Journal, 47(2):132-140.
Sittig et al. (2016) "Genetic Background Limits Generalizability of Genotype-Phenotype Relationships," Neuron, 91 (6):1253-1359.
Zhu et al. (2019) "Humanising the mouse genome piece by piece," Nature Communications, 10(1845):1-13.
Statement of Relatedness under MPEP 2001.06 with Respect to U.S. Appl. No. 16/184,473 dated Nov. 30, 2020.

\* cited by examiner

GENETICALLY MODIFIED MAJOR HISTOCOMPATIBILITY COMPLEX MICE

CROSS REFERENCE TO RELATED APPLICATIONS

This application is a continuation application of U.S. application Ser. No. 14/185,316, filed Feb. 20, 2014, which application claims benefit under 35 U.S.C. § 119(e) of U.S. provisional patent application Ser. No. 61/767,811, filed Feb. 22, 2013, each of which applications is hereby incorporated by reference in its entirety.

SEQUENCE LISTING

The present specification makes reference to a sequence listing submitted in electronic Form as an ascii .txt file named "2010794-0442_ST25" on Feb. 20, 2014. The .txt file was generated on Feb. 20, 2014 and is 8 kb in size.

FIELD OF THE INVENTION

Present invention relates to a genetically modified non-human animal, e.g., a rodent (e.g., a mouse or a rat), that expresses a human or humanized Major Histocompatibility Complex (MHC) class I and a human or humanized MHC class II molecules. The invention also relates to a genetically modified non-human animal, e.g., a mouse or a rat, that expresses a human or humanized MHC I protein (e.g., MHC I α chain) and a human or humanized MHC II protein (e.g., MHC II α and MHC II β chains), and further expresses a human or humanized β2 microglobulin; as well as embryos, tissues, and cells expressing the same. The invention further provides methods for making a genetically modified non-human animal that expresses both human or humanized MHC class I and class II proteins, and/or β2 microglobulin. Also provided are methods for identifying and evaluating peptides in the context of a humanized cellular immune system in vitro or in a genetically modified non-human animal, and methods of modifying an MHC locus of a non-human animal, e.g., a mouse or a rat, to express a human or humanized MHC I and a human or humanized MHC II proteins.

BACKGROUND OF THE INVENTION

In the adaptive immune response, foreign antigens are recognized by receptor molecules on B lymphocytes (e.g., immunoglobulins) and T lymphocytes (e.g., T cell receptor or TCR). These foreign antigens are presented on the surface of cells as peptide fragments by specialized proteins, generically referred to as major histocompatibility complex (MHC) molecules. MHC molecules are encoded by multiple loci that are found as a linked cluster of genes that spans about 4 Mb. In mice, the MHC genes are found on chromosome 17, and for historical reasons are referred to as the histocompatibility 2 (H-2) genes. In humans, the genes are found on chromosome 6 and are called human leukocyte antigen (HLA) genes. The loci in mice and humans are polygenic; they include three highly polymorphic classes of MHC genes (class I, II and III) that exhibit similar organization in human and murine genomes (see FIG. 2 and FIG. 3, respectively).

MHC loci exhibit the highest polymorphism in the genome; some genes are represented by >300 alleles (e.g., human HLA-DRβ and human HLA-B). All class I and II MHC genes can present peptide fragments, but each gene expresses a protein with different binding characteristics, reflecting polymorphisms and allelic variants. Any given individual has a unique range of peptide fragments that can be presented on the cell surface to B and T cells in the course of an immune response.

Both humans and mice have class I MHC genes (see FIG. 2 and FIG. 3). In humans, the classical class I genes are termed HLA-A, HLA-B and HLA-C, whereas in mice they are H-2K, H-2D and H-2L. Class I molecules consist of two chains: a polymorphic α-chain (sometimes referred to as heavy chain) and a smaller chain called β2-microglobulin (also known as light chain), which is generally not polymorphic (FIG. 1, left). These two chains form a non-covalent heterodimer on the cell surface. The α-chain contains three domains (α1, α2 and α3). Exon 1 of the α-chain gene encodes the leader sequence, exons 2 and 3 encode the α1 and α2 domains, exon 4 encodes the α3 domain, exon 5 encodes the transmembrane domain, and exons 6 and 7 encode the cytoplasmic tail. The α-chain forms a peptide-binding cleft involving the α1 and α2 domains (which resemble Ig-like domains) followed by the α3 domain, which is similar to β2-microglobulin.

β2 microglobulin is a non-glycosylated 12 kDa protein; one of its functions is to stabilize the MHC class I α-chain. Unlike the α-chain, the β2 microglobulin does not span the membrane. The human β2 microglobulin locus is on chromosome 15, while the mouse locus is on chromosome 2. The β2 microglobulin gene consists of 4 exons and 3 introns. Circulating forms of β2 microglobulin are present in serum, urine, and other body fluids; non-covalently MHC I-associated β2 microglobulin can be exchanged with circulating β2 microglobulin under physiological conditions.

Class I MHC molecules are expressed on all nucleated cells, including tumor cells. They are expressed specifically on T and B lymphocytes, macrophages, dendritic cells and neutrophils, among other cells, and function to display peptide fragments (typically 8-10 amino acids in length) on the surface to CD8+ cytotoxic T lymphocytes (CTLs). CTLs are specialized to kill any cell that bears an MHC I-bound peptide recognized by its own membrane-bound TCR. When a cell displays peptides derived from cellular proteins not normally present (e.g., of viral, tumor, or other non-self origin), such peptides are recognized by CTLs, which become activated and kill the cell displaying the peptide.

Both humans and mice also have class II MHC genes (see FIGS. 2 and 3). In humans, the classical MHC II genes are termed HLA-DP, HLA-DQ, and HLA-DR, whereas in mice they are H-2A and H-2E (often abbreviated as I-A and I-E, respectively). Additional proteins encoded by genes in the MHC II locus, HLA-DM and HLA-DO in humans, and H-2M and H-2O in mice, are not found on the cell surface, but reside in the endocytic compartment and ensure proper loading of MHC II molecules with peptides. Class II molecules consist of two polypeptide chains: α chain and β chain. The extracellular portion of the α chain contains two extracellular domains, α1 and α2; and the extracellular portion of the β chain also contains two extracellular domains, β1 and β2 (see FIG. 1, right). The α and the β chains are non-covalently associated with each other.

MHC class II molecules are expressed on antigen-presenting cells (APCs), e.g., B cells, macrophages, dendritic cells, endothelial cells during a course of inflammation, etc. MHC II molecules expressed on the surface of APCs typically present antigens generated in intracellular vesicles to CD4+ T cells. In order to participate in CD4+ T cell engagement, the MHC class II complex with the antigen of interest must be sufficiently stable to survive long enough to engage a CD4+ T cell. When a CD4+ T helper cell is engaged by a foreign peptide/MHC II complex on the surface of APC, the T cell is activated to release cytokines that assist in immune response to the invader.

Not all antigens will provoke T cell activation due to tolerance mechanisms. However, in some diseases (e.g., cancer, autoimmune diseases) peptides derived from self-proteins become the target of the cellular component of the immune system, which results in destruction of cells presenting such peptides. There has been significant advancement in recognizing antigens that are clinically significant (e.g., antigens associated with various types of cancer). However, in order to improve identification and selection of peptides that will provoke a suitable response in a human T cell, in particular for peptides of clinically significant antigens, there remains a need for in vivo and in vitro systems that mimic aspects of human immune system. Thus, there is a need for biological systems (e.g., genetically modified non-human animals and cells) that can display components of a human immune system.

SUMMARY OF THE INVENTION

A biological system for generating or identifying peptides that associate with human MHC class I proteins and chimeras thereof and bind CD8+ T cells, as well as peptides that associate with human MHC class II proteins and chimeras thereof and bind to CD4+ T cells, is provided. Non-human animals comprising non-human cells that express humanized molecules that function in the cellular immune response are provided. Humanized rodent loci that encode humanized MHC I and MHC II proteins are also provided. Humanized rodent cells that express humanized MHC molecules are also provided. In vivo and in vitro systems are provided that comprise humanized rodent cells, wherein the rodent cells express one or more humanized immune system molecules.

In various embodiments, provided herein is a non-human animal comprising at an endogenous MHC locus a first nucleotide sequence encoding a chimeric human/non-human MHC I polypeptide, wherein a human portion of the chimeric MHC I polypeptide comprises an extracellular domain of a human MHC I polypeptide; a second nucleotide sequence encoding a chimeric human/non-human MHC II α polypeptide, wherein a human portion of the chimeric human/non-human MHC II α polypeptide comprises an extracellular domain of a human MHC II α polypeptide; and a third nucleotide sequence encoding a chimeric human/non-human MHC II β polypeptide, wherein a human portion of the chimeric human/non-human MHC II β polypeptide comprises an extracellular domain of a human MHC II β polypeptide, wherein the non-human animal expresses functional chimeric human/non-human MHC I and MHC II proteins from its endogenous non-human MHC locus. In one embodiment, the animal does not express functional endogenous MHC I, II α, and/or II β polypeptides from the endogenous non-human MHC locus.

In one aspect, the first nucleotide sequence is located at the endogenous non-human MHC I locus, the second nucleotide sequence is located at the endogenous non-human MHC II α locus, and the third nucleotide sequence is located at the endogenous non-human MHC II β locus. In one aspect, the first, second and/or third nucleotide sequence(s) are operably linked to endogenous non-human regulatory elements. In one aspect, the first nucleotide sequence is operably linked to endogenous non-human MHC I promoter and regulatory elements, the second nucleotide sequence is operably linked to endogenous non-human MHC II α promoter and regulatory elements, and the third nucleotide sequence is operably linked to endogenous non-human MHC II β promoter and regulatory elements.

In one embodiment, the human portion of a chimeric MHC I polypeptide comprises α1, α2, and α3 domains of the human MHC I polypeptide. In one aspect, a non-human portion of the chimeric MHC I polypeptide comprises transmembrane and cytoplasmic domains of an endogenous non-human MHC I polypeptide. The human MHC I polypeptide may be selected from the group consisting of HLA-A, HLA-B, and HLA-C. In one embodiment, the human MHC I polypeptide is HLA-A2. In another aspect, the human MHC I polypeptide is HLA-A3, HLA-B7, HLA-B27, HLA-Cw6, or any other MHC I molecule expressed in a human population. In an additional embodiment, a non-human animal of the invention further comprises at its endogenous non-human β2 microglobulin locus a nucleotide sequence encoding a human or humanized β2 microglobulin polypeptide, wherein the animal expresses the human or humanized β2 microglobulin polypeptide.

In one embodiment, the human MHC II α extracellular domain comprises human MHC II α1 and α2 domains. In another embodiment, the human MHC II β extracellular domain comprises human MHC II β1 and β2 domains. In one aspect, the non-human portion of a chimeric human/non-human MHC II α polypeptide comprises transmembrane and cytoplasmic domains of an endogenous non-human MHC II α polypeptide. In one aspect, the non-human portion of a chimeric human/non-human MHC II β polypeptide comprises transmembrane and cytoplasmic domains of an endogenous non-human MHC II β polypeptide. In one embodiment, the human portions of a chimeric human/mouse MHC II α and β polypeptides are derived from a human HLA class II protein selected from the group consisting of HLA-DR, HLA-DQ, and HLA-DP. In one specific embodiment, the human portions of chimeric human/non-human MHC II α and β polypeptides are derived from a human HLA-DR4 protein. Alternatively, the human portions of chimeric human/non-human MHC II α and β polypeptides may be derived from human MHC II protein selected from HLA-DR2, HLA-DQ2.5, HLA-DQ8, or any other MHC II molecule expressed in a human population.

In some aspects, a provided animal comprises two copies of the MHC locus containing the first, the second, and the third nucleotide sequences, while in other aspects, a provided animal comprises one copy of the MHC locus containing the first, the second, and the third nucleotide sequences. Thus, the animal may be homozygous or heterozygous for the MHC locus containing nucleotide sequences encoding chimeric human/non-human MHC I, MHC II α, and MHC II β polypeptides. In some embodiments of the invention, the genetically modified MHC locus, comprising nucleotide sequences encoding chimeric human/non-human MHC I, MHC II α, and MHC II β polypeptides described herein, is in the germline of the non-human animal.

Also provided herein is an MHC locus comprising a first nucleotide sequence encoding a chimeric human/non-human MHC I polypeptide, wherein a human portion of the chimeric MHC I polypeptide comprises an extracellular domain of a human MHC I polypeptide; a second nucleotide sequence encoding a chimeric human/non-human MHC II α polypeptide, wherein a human portion of the chimeric human/non-human MHC II α polypeptide comprises an extracellular domain of a human MHC II α polypeptide; and a third nucleotide sequence encoding a chimeric human/non-human MHC II β polypeptide, wherein a human portion of the chimeric human/non-human MHC II β polypeptide comprises an extracellular domain of a human MHC II β polypeptide. In some aspects, non-human portions of the chimeric MHC I, II α, and II β polypeptides comprise transmembrane and cytoplasmic domains of non-human MHC I, II α, and II β, respectively.

In one embodiment, the genetically engineered non-human animal is a rodent. In one embodiment, the rodent is a rat or a mouse. In one embodiment, the rodent is a mouse. Thus, in one aspect, the first nucleotide sequence encodes a chimeric human/mouse MHC I polypeptide, and the mouse portion of the chimeric MHC I polypeptide is derived from H-2K, H-2D, or H-2L. In one specific embodiment, the mouse portion of the chimeric MHC I polypeptide is derived from H-2K. In one aspect, the second nucleotide sequence encodes a chimeric human/mouse MHC II α polypeptide, the third nucleotide sequence encodes a chimeric human/mouse MHC II β polypeptide, and the mouse portions of the chimeric MHC II α and β polypeptides are derived from H-2E or H-2A. In a specific embodiment, the mouse portions of the chimeric MHC II polypeptides are derived from H-2E.

Thus, also provided herein is a genetically engineered mouse comprising at an endogenous MHC locus a first nucleotide sequence encoding a chimeric human/mouse MHC I polypeptide, wherein the human portion of the chimeric MHC I polypeptide comprises an extracellular domain of a human MHC I polypeptide; a second nucleotide sequence encoding a chimeric human/mouse MHC II α polypeptide, wherein the human portion of the chimeric human/non-human MHC II α polypeptide comprises an extracellular domain of a human MHC II α polypeptide; and a third nucleotide sequence encoding a chimeric human/mouse MHC II β polypeptide, wherein the human portion of the chimeric human/non-human MHC II β polypeptide comprises an extracellular domain of a human MHC II β polypeptide; wherein the mouse expresses functional chimeric human/mouse MHC I and MHC II proteins from its endogenous mouse MHC locus. In one specific embodiment, the first nucleotide sequence encodes a chimeric HLA-A2/H-2K polypeptide, the second nucleotide sequence encodes an α chain of a chimeric HLA-DR4/H-2E polypeptide, and the third nucleotide sequence encodes a β chain of a chimeric HLA-DR4/H-2E polypeptide, and the mouse expresses functional HLA-A2/H-2K and HLA-DR4/H-2E proteins. In an additional embodiment, the mouse further comprises at an endogenous β2 microglobulin locus a nucleotide sequence encoding a human or humanized β2 microglobulin polypeptide. In one embodiment, the mouse does not express functional endogenous MHC polypeptides from its endogenous MHC locus.

Also provided herein are methods for generating a genetically modified non-human animal (e.g., rodent, e.g., mouse or rat) described herein. Thus, in one aspect, the invention provides a method of generating a genetically modified non-human animal comprising replacing at an endogenous non-human MHC II locus a nucleotide sequence encoding a non-human MHC II complex with a nucleotide sequence encoding a chimeric human/non-human MHC II complex to generate a first non-human animal; and replacing at an endogenous non-human MHC I locus a nucleotide sequence encoding a non-human MHC I polypeptide with a nucleotide sequence encoding a chimeric human/non-human MHC I polypeptide to generate a second non-human animal. In one aspect, the steps of replacing nucleotide sequences comprise homologous recombination in non-human ES cells, and the second non-human animal is generated by homologous recombination in ES cells bearing nucleotide sequences encoding chimeric human/non-human MHC II complex. The chimeric MHC II complex comprises chimeric human/non-human MHC II α and β polypeptides.

In an alternative embodiment, the invention provides a method of generating a genetically modified non-human animal comprising replacing at an endogenous non-human MHC I locus a nucleotide sequence encoding a non-human MHC I polypeptide with a nucleotide sequence encoding a chimeric human/non-human MHC I polypeptide to generate a first non-human animal; and replacing at an endogenous non-human MHC II locus a nucleotide sequence encoding a non-human MHC II complex with a nucleotide sequence encoding a chimeric human/non-human MHC II complex to generate a second non-human animal. In one aspect, the steps of replacing nucleotide sequences comprise homologous recombination in non-human ES cells, and the second non-human animal is generated by homologous recombination in ES cells bearing a nucleotide sequence encoding chimeric human/non-human MHC I polypeptide.

Also provided herein are cells, e.g., isolated antigen-presenting cells, derived from the non-human animals (e.g., rodents, e.g., mice or rats) described herein. Tissues and embryos derived from the non-human animals described herein are also provided.

Any of the embodiments and aspects described herein can be used in conjunction with one another, unless otherwise indicated or apparent from the context. Other embodiments will become apparent to those skilled in the art from a review of the ensuing detailed description. The following detailed description includes exemplary representations of various embodiments of the invention, which are not restrictive of the invention as claimed. The accompanying figures constitute a part of this specification and, together with the description, serve only to illustrate embodiments and not to limit the invention.

EP=electroporation. Triangles represent exons, filled triangles represent mouse exons from C57BL/6 mouse (with the exception of hashed triangles, which represent exon 1 of I-Eα from BALB/c mouse) and open triangles represent human exons.

Figure 6:
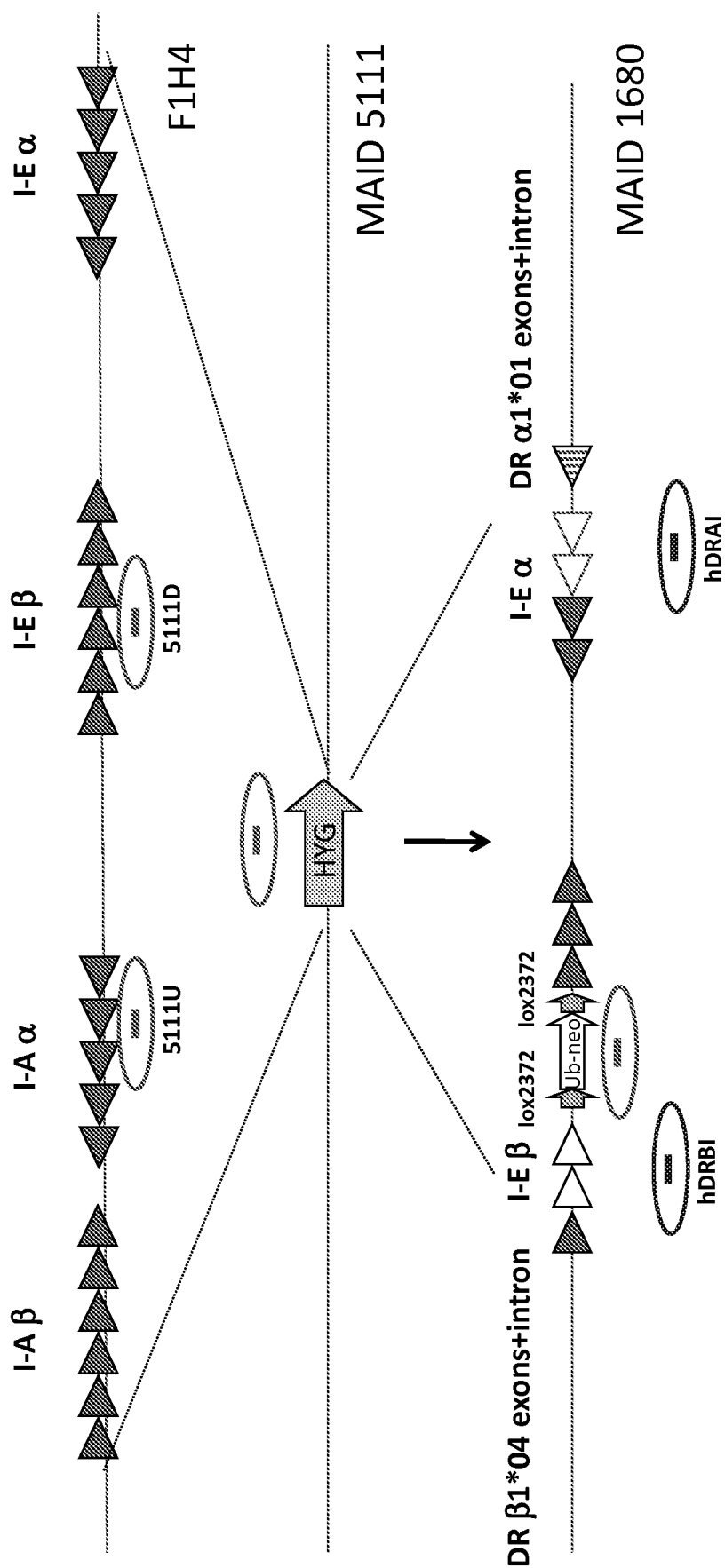

FIG. 6 shows a schematic illustration, not to scale, of MHC class II I-E and I-A genes, showing knockout of the mouse locus using a hygromycin cassette, followed by introduction of a vector comprising a humanized I-E β and I-E α (i.e., H-2Eβ/HLA-DRβ1*04 and H-2Eα/HLA-DRα*01 chimera, respectively). Open triangles represent human exons; filled triangles represent mouse exons. Probes used for genotyping are encircled.

Figure 7:
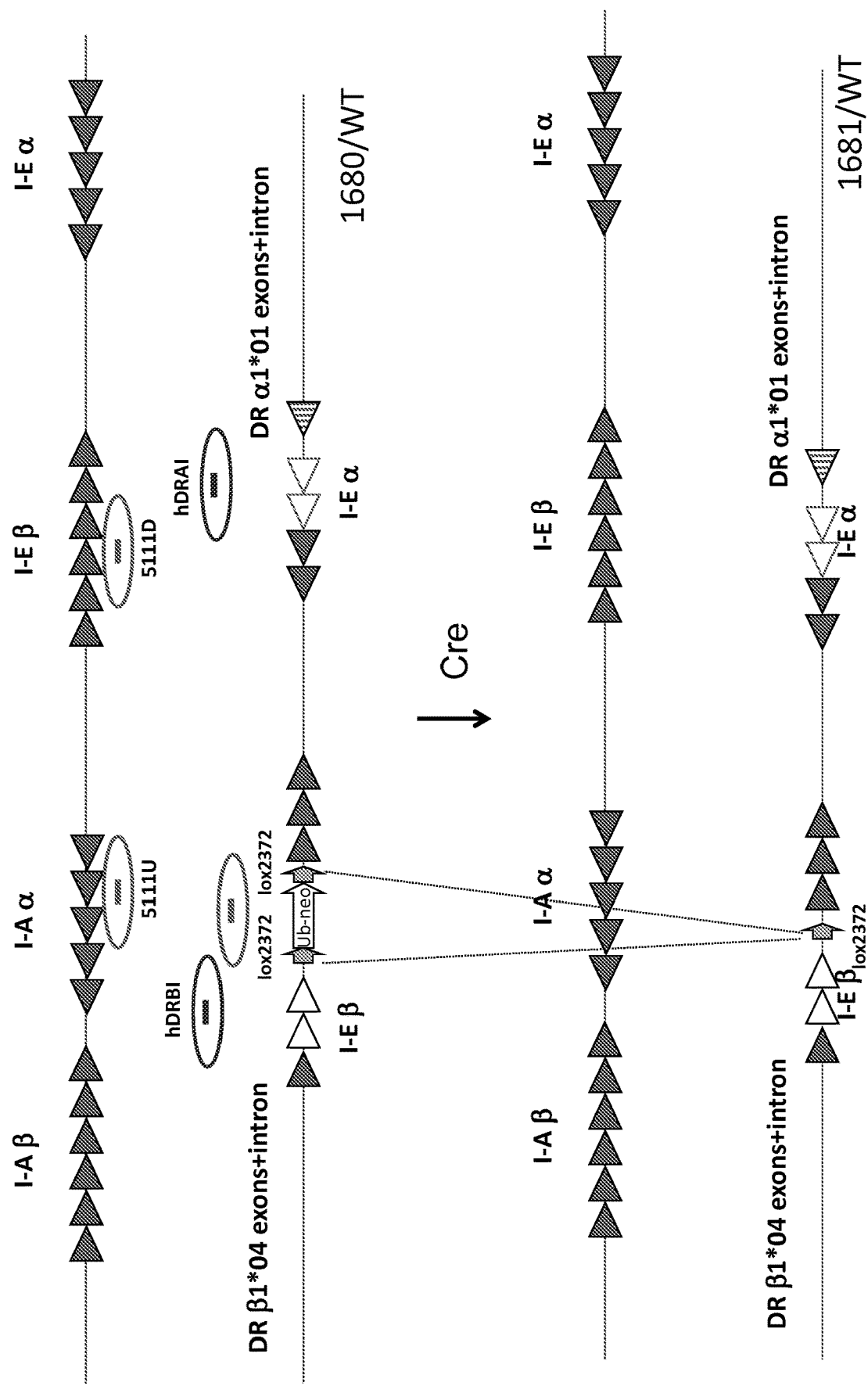

FIG. 7 shows a schematic illustration, not to scale, of Cre-mediated removal of the neomycin cassette of FIG. 6. Open triangles represent human exons; filled triangles represent mouse exons. Top two strands represent MHC II loci in humanized MHC II heterozygous mouse harboring a neomycin selection cassette, and bottom two strands represent MHC II loci in humanized MHC II heterozygous mouse with neomycin cassette removed.

Figure 8:
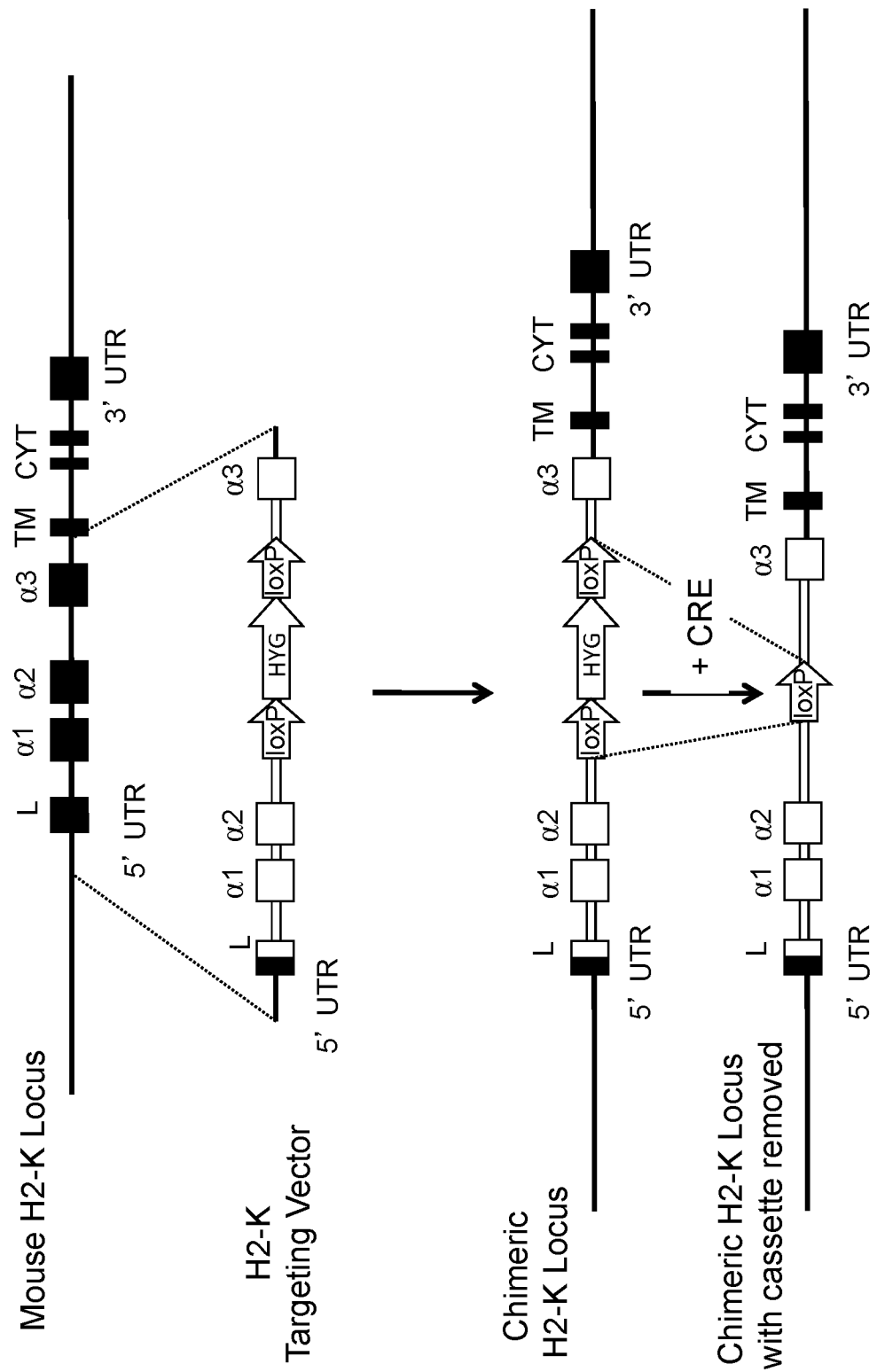

FIG. 8 is a schematic diagram (not to scale) of the targeting strategy used for making a chimeric H-2K locus that expresses an extracellular region of a human HLA-A2 protein. Mouse sequences are represented in black and human sequences are represented in white. L=leader, UTR=untranslated region, TM=transmembrane domain, CYT=cytoplasmic domain, HYG=hygromycin.

Figure 9:
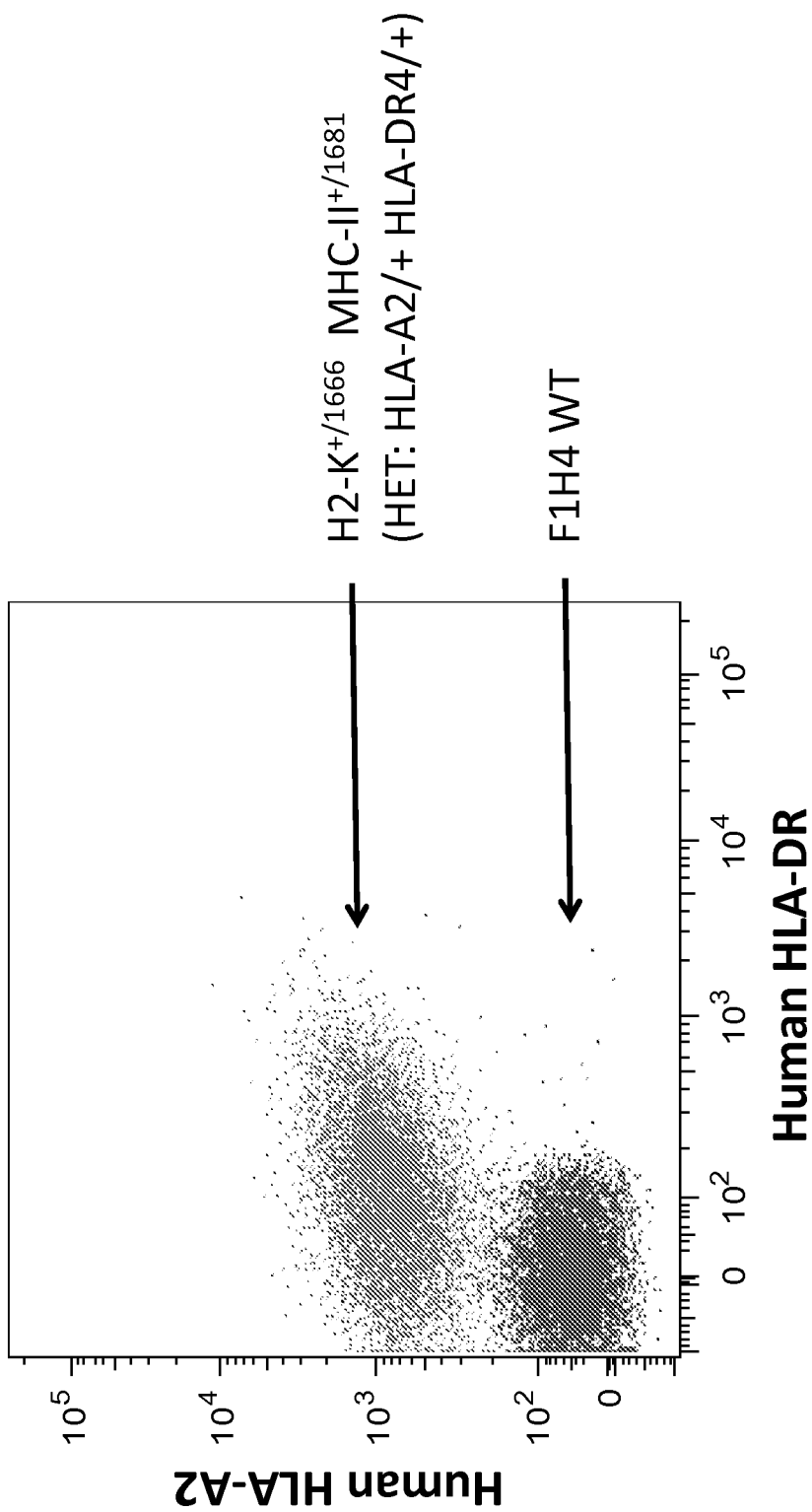

FIG. 9 is a dot plot of in vivo expression of HLA-A2 and HLA-DR4 in heterozygous mice harboring chimeric HLA-A2/H-2K and HLA-DR4/H-2E loci. Steady state HLA-DR4 expression was low but present; this low expression was expected and the expression gets upregulated upon activation.

DETAILED DESCRIPTION OF EMBODIMENTS OF THE INVENTION

Definitions

The present invention provides genetically modified non-human animals (e.g., mice, rats, rabbits, etc.) that express both human or humanized MHC I and MHC II proteins; embryos, cells, and tissues comprising the same; methods of making the same; as well as methods of using the same. Unless defined otherwise, all terms and phrases used herein include the meanings that the terms and phrases have attained in the art, unless the contrary is clearly indicated or clearly apparent from the context in which the term or phrase is used.

The term "conservative," when used to describe a conservative amino acid substitution, includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of MHC I or MHC II to present a peptide of interest. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database, Science 256:1443-45), hereby incorporated by reference. In some embodiments, the substitution is a moderately conservative substitution wherein the substitution has a nonnegative value in the PAM250 log-likelihood matrix.

Thus, also encompassed by the invention is a genetically modified non-human animal whose genome comprises a nucleotide sequence encoding a human or humanized MHC I and II polypeptides, wherein MHC I or MHC II the polypeptide comprises conservative amino acid substitutions in the amino acid sequence described herein.

One skilled in the art would understand that in addition to the nucleic acid residues encoding a human or humanized MHC I or MHC II polypeptide described herein, due to the degeneracy of the genetic code, other nucleic acids may encode the polypeptide of the invention. Therefore, in addition to a genetically modified non-human animal that comprises in its genome a nucleotide sequence encoding MHC I and MHC II polypeptides with conservative amino acid substitutions, a non-human animal whose genome comprises a nucleotide sequence that differs from that described herein due to the degeneracy of the genetic code is also provided.

The term "identity" when used in connection with sequence includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences. In various embodiments, identity is determined by comparing the sequence of a mature protein from its N-terminal to its C-terminal. In various embodiments when comparing a chimeric human/non-human sequence to a human sequence, the human portion of the chimeric human/non-human sequence (but not the non-human portion) is used in making a comparison for the purpose of ascertaining a level of identity between a human sequence and a human portion of a chimeric human/non-human sequence (e.g., comparing a human ectodomain of a chimeric human/mouse protein to a human ectodomain of a human protein).

The terms "homology" or "homologous" in reference to sequences, e.g., nucleotide or amino acid sequences, means two sequences which, upon optimal alignment and comparison, are identical in at least about 75% of nucleotides or amino acids, e.g., at least about 80% of nucleotides or amino acids, e.g., at least about 90-95% nucleotides or amino acids, e.g., greater than 97% nucleotides or amino acids. One skilled in the art would understand that, for optimal gene targeting, the targeting construct should contain arms homologous to endogenous DNA sequences (i.e., "homology arms"); thus, homologous recombination can occur between the targeting construct and the targeted endogenous sequence.

The term "operably linked" refers to a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. In addition, various portions of the chimeric or humanized protein of the invention may be operably linked to retain proper folding, processing, targeting, expression, and other functional properties of the protein in the cell. Unless stated otherwise, various domains of the chimeric or humanized protein of the invention are operably linked to each other.

The term "MHC I complex" or the like, as used herein, includes the complex between the MHC I α chain polypeptide and the β2-microglobulin polypeptide. The term "MHC I polypeptide" or the like, as used herein, includes the MHC I α chain polypeptide alone. The terms "MHC II complex," "MHC II protein," or the like, as used herein, include the complex between an MHC II α polypeptide and an MHC II β polypeptide. The term "MHC II α polypeptide" or "MHC II β polypeptide" (or the like), as used herein, includes the MHC II α polypeptide alone or MHC II β polypeptide alone, respectively. Similarly, the terms "HLA-DR4 complex", "HLA-DR4 protein," "H-2E complex," "H-2E" protein," or the like, refer to complex between α and β polypeptides. Typically, the terms "human MHC" and "HLA" are used interchangeably.

The term "replacement" in reference to gene replacement refers to placing exogenous genetic material at an endogenous genetic locus, thereby replacing all or a portion of the endogenous gene with an orthologous or homologous nucleic acid sequence. As demonstrated in the Examples below, nucleic acid sequence of endogenous MHC locus was replaced by a nucleotide sequence comprising sequences encoding a portion of human MHC I polypeptide, specifically, encoding the extracellular portion of the MHC I polypeptide; as well as portions of human MHC II α and β polypeptides, specifically, encoding the extracellular portions of the MHC II α and β polypeptides.

"Functional" as used herein, e.g., in reference to a functional polypeptide, refers to a polypeptide that retains at least one biological activity normally associated with the native protein. For example, in some embodiments of the invention, a replacement at an endogenous locus (e.g., replacement at an endogenous non-human MHC locus) results in a locus that fails to express a functional endogenous polypeptide, e.g., MHC I or MHC II polypeptide. Likewise, the term "functional" as used herein in reference to functional extracellular domain of a protein, refers to an extracellular domain that retains its functionality, e.g., in the case of MHC I or MHC II, ability to bind an antigen, ability to bind a T cell co-receptor, etc. In some embodiments of the invention, a replacement at the endogenous MHC locus results in a locus that fails to express an extracellular domain (e.g., a functional extracellular domain) of an endogenous MHC while expressing an extracellular domain (e.g., a functional extracellular domain) of a human MHC.

Genetically Modified MHC Animals

In various embodiments, the invention generally provides genetically modified non-human animals that comprise in their genome a nucleotide sequence encoding a human or humanized MHC I and MHC II polypeptides; thus, the animals express a human or humanized MHC I and MHC II polypeptides.

Figure 2:
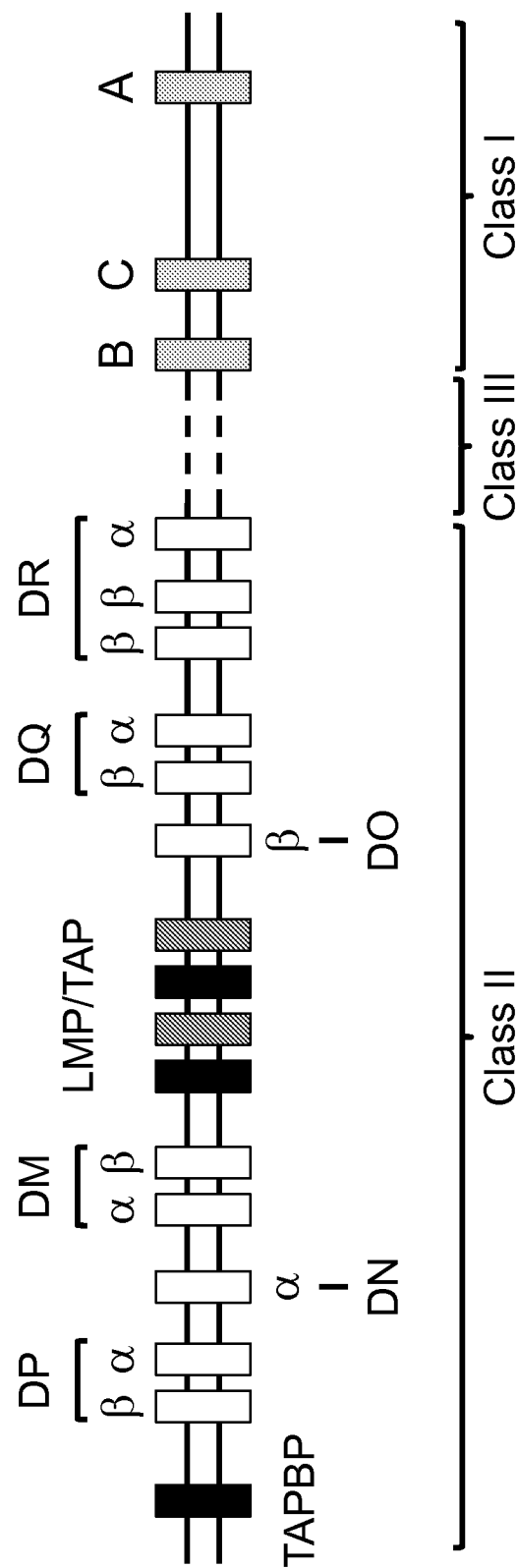
FIG. 2 is a schematic representation (not to scale) of the relative genomic structure of the human HLA, showing class I, II and III genes.
Figure 3:
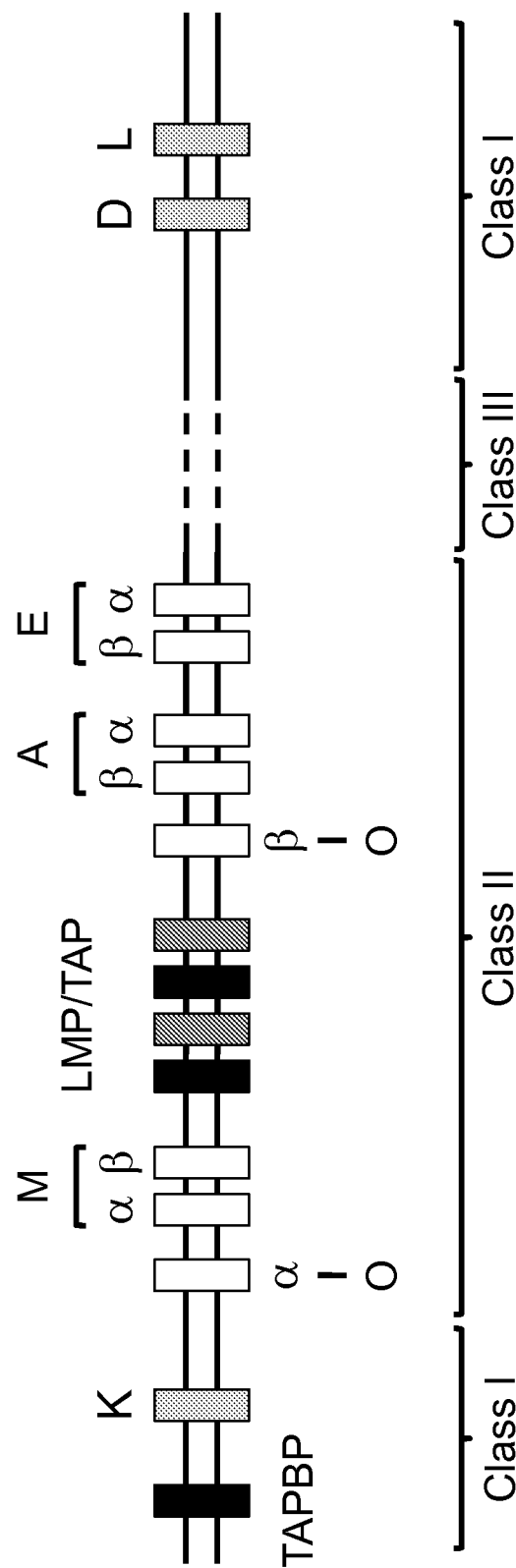
FIG. 3 is a schematic representation (not to scale) of the relative genomic structure of the mouse MHC, showing class I, II and III genes.

MHC genes are categorized into three classes: class I, class II, and class III, all of which are encoded either on human chromosome 6 or mouse chromosome 17. A schematic of the relative organization of the human and mouse MHC classes is presented in FIGS. 2 and 3, respectively. The MHC genes are among the most polymorphic genes of the mouse and human genomes. MHC polymorphisms are presumed to be important in providing evolutionary advantage; changes in sequence can result in differences in peptide binding that allow for better presentation of pathogens to cytotoxic T cells.

MHC class I protein comprises an extracellular domain (which comprises three domains: $\alpha_1$, $\alpha_2$, and $\alpha_3$), a transmembrane domain, and a cytoplasmic tail. The $\alpha_1$ and $\alpha_2$ domains form the peptide-binding cleft, while the $\alpha_3$ interacts with β2-microglobulin.

In addition to its interaction with β2-microglobulin, the $\alpha_3$ domain interacts with the TCR co-receptor CD8, facilitating antigen-specific activation. Although binding of MHC class I to CD8 is about 100-fold weaker than binding of TCR to MHC class I, CD8 binding enhances the affinity of TCR binding. Wooldridge et al. (2010) MHC Class I Molecules with Superenhanced CD8 Binding Properties Bypass the Requirement for Cognate TCR Recognition and Nonspecifically Activate CTLs, J. Immunol. 184:3357-3366. Interestingly, increasing MHC class I binding to CD8 abrogated antigen specificity in CTL activation. Id.

CD8 binding to MHC class I molecules is species-specific; the mouse homolog of CD8, Lyt-2, was shown to bind $H-2D^d$ molecules at the α3 domain, but it did not bind HLA-A molecules. Connolly et al. (1988) The Lyt-2 Molecule Recognizes Residues in the Class I α3 Domain in Allogeneic Cytotoxic T Cell Responses, J. Exp. Med. 168: 325-341. Differential binding was presumably due to CDR-like determinants (CDR1- and CDR2-like) on CD8 that was not conserved between humans and mice. Sanders et al. (1991) Mutations in CD8 that Affect Interactions with HLA Class I and Monoclonal Anti-CD8 Antibodies, J. Exp. Med. 174:371-379; Vitiello et al. (1991) Analysis of the HLA-restricted Influenza-specific Cytotoxic T Lymphocyte Response in Transgenic Mice Carrying a Chimeric Human-Mouse Class I Major Histocompatibility Complex, J. Exp. Med. 173:1007-1015; and, Gao et al. (1997) Crystal structure of the complex between human CD8αα and HLA-A2, Nature 387:630-634. It has been reported that CD8 binds HLA-A2 in a conserved region of the α3 domain (at position 223-229). A single substitution (V245A) in HLA-A reduced binding of CD8 to HLA-A, with a concomitant large reduction in T cell-mediated lysis. Salter et al. (1989), Polymorphism in the α3 domain of HLA-A molecules affects binding to CD8, Nature 338:345-348. In general, polymorphism in the α3 domain of HLA-A molecules also affected binding to CD8. Id. In mice, amino acid substitution at residue 227 in $H-2D^d$ affected the binding of mouse Lyt-2 to $H-2D^d$, and cells transfected with a mutant $H-2D^d$ were not lysed by CD8+ T cells. Potter et al. (1989) Substitution at residue 227 of H-2 class I molecules abrogates recognition by CD8-dependent, but not CD8-independent, cytotoxic T lymphocytes, Nature 337:73-75.

Therefore, due to species specificity of interaction between the MHC class I α3 domain and CD8, an MHC I complex comprising a replacement of an H-2K α3 domain with a human HLA-A2 α3 domain was nonfunctional in a mouse (i.e., in vivo) in the absence of a human CD8. In animals transgenic for HLA-A2, substitution of human α3 domain for the mouse α3 domain resulted in restoration of T cell response. Irwin et al. (1989) Species-restricted interactions between CD8 and the α3 domain of class I influence the magnitude of the xenogeneic response, J. Exp. Med. 170:1091-1101; Vitiello et al. (1991), supra.

The transmembrane domain and cytoplasmic tail of mouse MHC class I proteins also have important functions. One function of MHC I transmembrane domain is to facilitate modulation by HLA-A2 of homotypic cell adhesion (to enhance or inhibit adhesion), presumably as the result of cross-linking (or ligation) of surface MHC molecules. Wagner et al. (1994) Ligation of MHC Class I and Class II Molecules Can Lead to Heterologous Desensitization of Signal Transduction Pathways That Regulate Homotypic Adhesion in Human Lymphocytes, J. Immunol. 152:5275-5287. Cell adhesion can be affected by mAbs that bind at diverse epitopes of the HLA-A2 molecule, suggesting that there are multiple sites on HLA-A2 implicated in modulating homotypic cell adhesion; depending on the epitope bound, the affect can be to enhance or to inhibit HLA-A2-dependent adhesion. Id.

The cytoplasmic tail, encoded by exons 6 and 7 of the MHC I gene, is reportedly necessary for proper expression on the cell surface and for LIR1-mediated inhibition of NK cell cytotoxicity. Gruda et al. (2007) Intracellular Cysteine Residues in the Tail of MHC Class I Proteins Are Crucial for Extracellular Recognition by Leukocyte Ig-Like Receptor 1, J. Immunol. 179:3655-3661. A cytoplasmic tail is required for multimerizaton of at least some MHC I molecules through formation of disulfide bonds on its cysteine residues, and thus may play a role in clustering and in recognition by NK cells. Lynch et al. (2009) Novel MHC Class I Structures on Exosomes, J. Immunol. 183:1884-1891.

The cytoplasmic domain of HLA-A2 contains a constitutively phosphorylated serine residue and a phosphorylatable tyrosine, although—in Jurkat cells—mutant HLA-A2 molecules lacking a cytoplasmic domain appear normal with respect to expression, cytoskeletal association, aggregation, and endocytic internalization. Gur et al. (1997) Structural Analysis of Class I MHC Molecules: The Cytoplasmic Domain Is Not Required for Cytoskeletal Association, Aggregation, and Internalization, Mol. Immunol. 34(2):125-132. Truncated HLA-A2 molecules lacking the cytoplasmic domain are apparently normally expressed and associate with β2 microglobulin. Id.

However, several studies have demonstrated that the cytoplasmic tail is critical in intracellular trafficking, dendritic cell (DC)-mediated antigen presentation, and CTL priming. A tyrosine residue encoded by exon 6 was shown to be required for MHC I trafficking through endosomal compartments, presentation of exogenous antigens, and CTL priming; while deletion of exon 7 caused enhancement of anti-viral CTL responses. Lizee et al. (2003) Control of Dendritic Cross-Presentation by the Major Histocompatibility Complex Class I Cytoplasmic Domain, Nature Immunol. 4:1065-73; Basha et al. (2008) MHC Class I Endosomal and Lysosomal Trafficking Coincides with Exogenous Antigen Loading in Dendritic Cells, PLoS ONE 3: e3247; and Rodriguez-Cruz et al. (2011) Natural Splice Variant of MHC Class I Cytoplasmic Tail Enhances Dendritic Cell-Induced CD8+ T-Cell Responses and Boosts Anti-Tumor Immunity, PLoS ONE 6:e22939.

Figure 1:
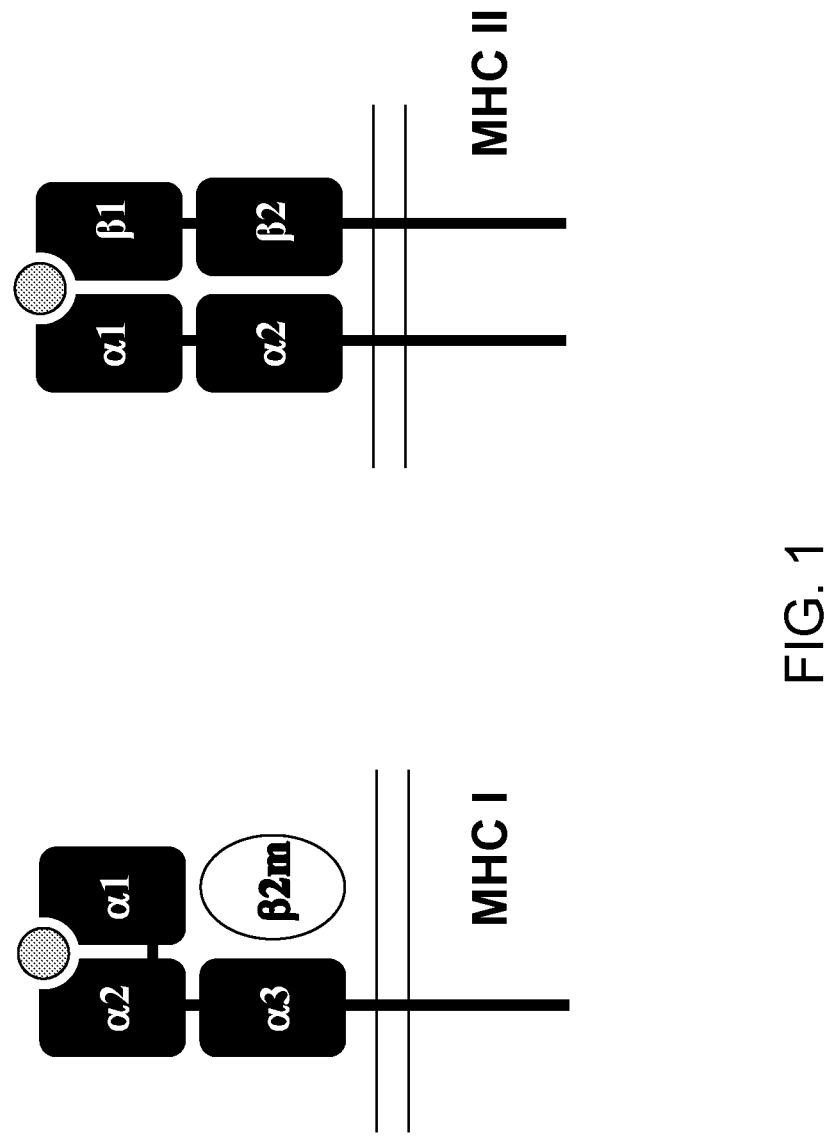
FIG. 1 is a schematic drawing of the MHC I (left panel) and MHC II (right panel) class molecules expressed on the surface of a cell. The gray circles represent peptides bound in the peptide-binding clefts.

MHC class II complex comprises two non-covalently associated domains: an α chain and a β chain, also referred herein as an α polypeptide and a β polypeptide (FIG. 1, right). The protein spans the plasma membrane; thus it contains an extracellular domain, a transmembrane domain, and a cytoplasmic domain. The extracellular portion of the α chain includes α1 and α2 domains, and the extracellular portion of the β chain includes β1 and β2 domains. The α1 and β1 domains form a peptide-binding cleft on the cell surface. Due to the three-dimensional conformation of the peptide-binding cleft of the MHC II complex, there is theoretically no upper limit on the length of the bound antigen, but typically peptides presented by MHC II are between 13 and 17 amino acids in length.

In addition to its interaction with the antigenic peptides, the peptide-binding cleft of the MHC II molecule interacts with invariant chain (Ii) during the processes of MHC II complex formation and peptide acquisition. The α/β MHC II dimers assemble in the endoplasmic reticulum and associate with Ii chain, which is responsible for control of peptide binding and targeting of the MHC II into endocytic pathway. In the endosome, Ii undergoes proteolysis, and a small fragment of Ii, Class II-associated invariant chain peptide (CLIP), remains at the peptide-binding cleft. In the endosome, under control of HLA-DM (in humans), CLIP is exchanged for antigenic peptides.

MHC II interacts with T cell co-receptor CD4 at the hydrophobic crevice at the junction between α2 and β2 domains. Wang and Reinherz (2002) Structural Basis of T Cell Recognition of Peptides Bound to MHC Molecules, Molecular Immunology, 38:1039-49. When CD4 and T cell receptor bind the same MHC II molecule complexed with a peptide, the sensitivity of a T cell to antigen is increased, and it requires 100-fold less antigen for activation. See, Janeway's Immunobiology, 7$^{th}$ Ed., Murphy et al. eds., Garland Science, 2008, incorporated herein by reference.

Numerous functions have been proposed for transmembrane and cytoplasmic domains of MHC II. In the case of cytoplasmic domain, it has been shown to be important for intracellular signaling, trafficking to the plasma membrane, and ultimately, antigen presentation. For example, it was shown that T cell hybridomas respond poorly to antigen-presenting cells (APCs) transfected with MHC II β chains truncated at the cytoplasmic domain, and induction of B cell differentiation is hampered. See, e.g., Smiley et al. (1996) Truncation of the class II β-chain cytoplasmic domain influences the level of class II/invariant chain-derived peptide complexes, Proc. Natl. Acad. Sci. USA, 93:241-44. Truncation of Class II molecules seems to impair cAMP production. It has been postulated that deletion of the cytoplasmic tail of MHC II affects intracellular trafficking, thus preventing the complex from coming across relevant antigens in the endocytic pathway. Smiley et al. (supra) demonstrated that truncation of class II molecules at the cytoplasmic domain reduces the number of CLIP/class II complexes, postulating that this affects the ability of CLIP to effectively regulate antigen presentation.

It has been hypothesized that, since MHC II clustering is important for T cell receptor (TCR) triggering, if MHC II molecules truncated at the cytoplasmic domain were prevented from binding cytoskeleton and thus aggregating, antigen presentation to T cells would be affected. Ostrand-Rosenberg et al. (1991) Abrogation of Tumorigenicity by MHC Class II Antigen Expression Requires the Cytoplasmic Domain of the Class II Molecule, J. Immunol. 147:2419-22. In fact, it was recently shown that HLA-DR truncated at the cytoplasmic domain failed to associate with the cytoskeleton following oligomerization. El Fakhy et al. (2004) Delineation of the HLA-DR Region and the Residues Involved in the Association with the Cytoskeleton, J. Biol. Chem. 279: 18472-80. Importantly, actin cytoskeleton is a site of localized signal transduction activity, which can effect antigen presentation. In addition to association with cytoskeleton, recent studies have also shown that up to 20% of all HLA-DR molecules constitutively reside in the lipid rafts of APCs, which are microdomains rich in cholesterol and glycosphingolipids, and that such localization is important for antigen presentation, immune synapse formation, and MHC II-mediated signaling. See, e.g., Dolan et al. (2004) Invariant Chain and the MHC II Cytoplasmic Domains Regulate Localization of MHC Class II Molecules to Lipid Rafts in Tumor Cell-Based Vaccines, J. Immunol. 172:907-14. Dolan et al. suggested that truncation of cytoplasmic domain of MHC II reduces constitutive localization of MHC II to lipid rafts.

In addition, the cytoplasmic domain of MHC II, in particular the β chain, contains a leucine residue that is subject to ubiquitination by ubiquitin ligase, membrane-associated RING-CH I (MARCH I), which controls endocytic trafficking, internalization, and degradation of MHC II; and it has been shown that MARCH-mediated ubiquitination ceases upon dendritic cell maturation resulting in increased levels of MHC II at the plasma membrane. Shin et al. (2006) Surface expression of MHC class II in dendritic cells is controlled by regulated ubiquitination, Nature 444: 115-18; De Gassart et al. (2008) MHC class II stabilization at the surface of human dendritic cells is the result of maturation-dependent MARCH I down-regulation, Proc. Natl. Acad. Sci. USA 105:3491-96.

Transmembrane domains of α and β chains of MHC II interact with each other and this interaction is important for proper assembly of class II MHC complex. Cosson and Bonifacino (1992) Role of Transmembrane Domain Interactions in the Assembly of Class II MHC Molecules, Nature 258:659-62. In fact, MHC II molecules in which the transmembrane domains of the α and β chains were replaced by the α chain of IL-2 receptor were retained in the ER and were barely detectable at the cell surface. Id. Through mutagenesis studies, conserved Gly residues at the α and β transmembrane domains were found to be responsible for MHC II assembly at the cell surface. Id. Thus, both transmembrane and cytoplasmic domains are crucial for the proper function of the MHC II complex.

In various embodiments, provided herein is a genetically modified non-human animal, e.g., rodent (e.g., mouse or rat) comprising in its genome a nucleotide sequence encoding a human or humanized MHC I polypeptide and a nucleotide sequence encoding human or humanized MHC II protein. The MHC I nucleotide sequence may encode an MHC I polypeptide that is partially human and partially non-human, e.g., chimeric human/non-human MHC I polypeptide, and the MHC II nucleotide sequence may encode an MHC II protein that is partially human and partially non-human, e.g., chimeric human/non-human MHC II protein (e.g., comprising chimeric human/non-human MHC II α and β polypeptides). In some aspects, the animal does not express endogenous MHC I and II polypeptides, e.g., functional endogenous MHC I and II polypeptides.

A genetically modified non-human animal comprising in its genome, e.g., at the endogenous locus, a nucleotide sequence encoding a chimeric human/non-human MHC I polypeptide is disclosed in U.S. patent application Ser. Nos. 13/661,159 and 13/793,812, which applications are incorporated herein by reference in their entireties. A genetically modified non-human animal comprising in its genome, e.g., at the endogenous locus, a nucleotide sequence encoding humanized, e.g., chimeric human/non-human MHC II polypeptides is disclosed in U.S. patent application Ser. Nos. 13/661,116 and 13/793,935, which applications are incorporated herein by reference in their entireties. Provided herein is a genetically modified non-human animal that comprises at its endogenous MHC locus a nucleotide sequence encoding a chimeric human/non-human MHC I polypeptide and chimeric human/non-human MHC II polypeptides. It would be difficult to generate such animal by simple breeding of humanized MHC I and MHC II animals due to the close linkage of MHC I and MHC II genes on mouse chromosome 17 and human chromosome 6. Therefore, the present application also provides a novel method for generating genetically modified non-human animals comprising sequences encoding human or humanized MHC I and MHC II polypeptides, e.g., animals in which sequences encoding endogenous MHC I and II polypeptides are replaced by those encoding chimeric human/non-human MHC I and II polypeptides.

Thus, in various embodiments provided herein is a genetically modified non-human animal comprising in its genome, e.g., at endogenous MHC locus, a first nucleotide sequence encoding a chimeric human/non-human MHC I polypeptide, wherein a human portion of the chimeric MHC I polypeptide comprises an extracellular domain of a human MHC I polypeptide; a second nucleotide sequence encoding a chimeric human/non-human MHC II α polypeptide, wherein a human portion of the chimeric MHC II α polypeptide comprises an extracellular domain of a human MHC II α polypeptide; and a third nucleotide sequence encoding a chimeric human/non-human MHC II β polypeptide, wherein a human portion of the chimeric MHC II β polypeptide comprises an extracellular domain of a human MHC II β polypeptide; wherein the non-human animal expresses functional chimeric human/non-human MHC I and MHC II proteins from its endogenous non-human MHC locus. In one embodiment, the first, second, and/or third nucleotide sequences are located the endogenous non-human MHC locus. In one embodiment, wherein the non-human animal is a mouse, the first, second, and/or third nucleotide sequences are located at the endogenous mouse MHC locus on mouse chromosome 17. In one embodiment, the first nucleotide sequence is located at the endogenous non-human MHC I locus. In one embodiment, the second nucleotide sequence is located at the endogenous non-human MHC II α locus. In one embodiment, the third nucleotide sequence is located at the endogenous non-human MHC II β locus.

In one embodiment, the non-human animal only expresses the chimeric human/non-human MHC I, MHC II α and/or MHC β II polypeptides and does not express endogenous non-human MHC polypeptides (e.g., functional endogenous MHC I, II α and/or II β polypeptides) from the endogenous non-human MHC locus. In one embodiment, the animal described herein expresses a functional chimeric MHC I and a functional chimeric MHC II on the surface of its cells, e.g., antigen presenting cells, etc.

In one embodiment, the chimeric human/non-human MHC I polypeptide comprises in its human portion a peptide binding domain of a human MHC I polypeptide. In one aspect, the human portion of the chimeric polypeptide comprises an extracellular domain of a human MHC I. In this embodiment, the human portion of the chimeric polypeptide comprises an extracellular domain of an α chain of a human MHC I. In one embodiment, the human portion of the chimeric polypeptide comprises α1 and α2 domains of a human MHC I. In another embodiment, the human portion of the chimeric polypeptide comprises α1, α2, and α3 domains of a human MHC I.

In one aspect, a human portion of the chimeric MHC II α polypeptide and/or a human portion of the chimeric MHC II β polypeptide comprises a peptide-binding domain of a human MHC II α polypeptide and/or human MHC II β polypeptide, respectively. In one aspect, a human portion of the chimeric MHC II α and/or β polypeptide comprises an extracellular domain of a human MHC II α and/or β polypeptide, respectively. In one embodiment, a human portion of the chimeric MHC II α polypeptide comprises α1 domain of a human MHC II α polypeptide; in another embodiment, a human portion of the chimeric MHC II α polypeptide comprises α1 and α2 domains of a human MHC II α polypeptide. In an additional embodiment, a human portion of the chimeric MHC II β polypeptide comprises β1 domain of a human MHC II β polypeptide; in another embodiment, a human portion of the chimeric MHC II β polypeptide comprises β1 and β2 domains of a human MHC II β polypeptide.

The human or humanized MHC I polypeptide may be derived from a functional human HLA molecule encoded by any of HLA-A, HLA-B, HLA-C, HLA-E, HLA-F, or HLA-G loci. The human or humanized MHC II polypeptide may be derived from a functional human HLA molecule encoded by an of HLA-DP, -DQ, and -DR loci. A list of commonly used HLA antigens and alleles is described in Shankarkumar et al. ((2004) The Human Leukocyte Antigen (HLA) System, Int. J. Hum. Genet. 4(2):91-103), incorporated herein by reference. Shankarkumar et al. also present a brief explanation of HLA nomenclature used in the art. Additional information regarding HLA nomenclature and various HLA alleles can be found in Holdsworth et al. (2009) The HLA dictionary 2008: a summary of HLA-A, -B, -C, -DRB1/3/4/5, and DQB1 alleles and their association with serologically defined HLA-A, -B, -C, -DR, and -DQ antigens, Tissue Antigens 73:95-170, and a recent update by Marsh et al. (2010) Nomenclature for factors of the HLA system, 2010, Tissue Antigens 75:291-455, both incorporated herein by reference. Thus, the human or humanized MHC I and/or II polypeptides may be derived from any functional human HLA molecules described therein.

Of particular interest are human HLA molecules, specific polymorphic HLA alleles, known to be associated with a number of human diseases, e.g., human autoimmune diseases. In fact, specific polymorphisms in HLA loci have been identified that correlate with development of rheumatoid arthritis, type I diabetes, Hashimoto's thyroiditis, multiple sclerosis, myasthenia gravis, Graves' disease, systemic lupus erythematosus, celiac disease, Crohn's disease, ulcerative colitis, and other autoimmune disorders. See, e.g., Wong and Wen (2004) What can the HLA transgenic mouse tell us about autoimmune diabetes?, Diabetologia 47:1476-87; Taneja and David (1998) HLA Transgenic Mice as Humanized Mouse Models of Disease and Immunity, J. Clin. Invest. 101:921-26; Bakker et al. (2006), A high-resolution HLA and SNP haplotype map for disease association studies in the extended human MHC, Nature Genetics 38:1166-72 and Supplementary Information; and International MHC and Autoimmunity Genetics Network (2009) Mapping of multiple susceptibility variants within the MHC region for 7 immune-mediated diseases, Proc. Natl. Acad. Sci. USA 106:18680-85. Thus, the human or humanized MHC I and/or II polypeptides may be derived from a human HLA molecule known to be associated with a particular disease, e.g., autoimmune disease.

In one specific aspect, the human or humanized MHC I polypeptide is derived from human HLA-A. In a specific embodiment, the HLA-A polypeptide is an HLA-A2 polypeptide (e.g., and HLA-A2.1 polypeptide). In one embodiment, the HLA-A polypeptide is a polypeptide encoded by an HLA-A*0201 allele, e.g., HLA-A*02:01:01:01 allele. The HLA-A*0201 allele is commonly used amongst the North American population. Although the present Examples describe this particular HLA sequence, any suitable HLA-A sequence is encompassed herein, e.g., polymorphic variants of HLA-A2 exhibited in human population, sequences with one or more conservative or non-conservative amino acid modifications, nucleic acid sequences differing from the sequence described herein due to the degeneracy of genetic code, etc.

In another specific aspect, the human portion of the chimeric MHC I polypeptide is derived from human MHC I selected from HLA-B and HLA-C. In one aspect, it is derived from HLA-B, e.g., HLA-B27. In another aspect, it is derived from HLA-A3, -B7, -Cw6, etc.

In one specific aspect, the human portions of the humanized MHC II α and β polypeptides described herein are derived from human HLA-DR, e.g., HLA-DR4. Typically, HLA-DR α chains are monomorphic, e.g., the α chain of HLA-DR complex is encoded by HLA-DRA gene (e.g., HLA-DRα*01 gene). On the other hand, the HLA-DR β chain is polymorphic. Thus, HLA-DR4 comprises an α chain encoded by HLA-DRA gene and a β chain encoded by HLA-DRB1 gene (e.g., HLA-DRβ1*04 gene). As described herein below, HLA-DR4 is known to be associated with incidence of a number of autoimmune diseases, e.g., rheumatoid arthritis, type I diabetes, multiple sclerosis, etc. In one embodiment of the invention, the HLA-DRA allele is HLA-DRα*01 allele, e.g., HLA-DRα*01:01:01:01. In another embodiment, the HLA-DRB allele is HLA-DRβ1*04, e.g., HLA-DRβ1*04:01:01. Although the present Examples describe these particular HLA sequences; any suitable HLA-DR sequences are encompassed herein, e.g., polymorphic variants exhibited in human population, sequences with one or more conservative or non-conservative amino acid modifications, nucleic acid sequences differing from the sequences described herein due to the degeneracy of genetic code, etc.

The human portions of the chimeric MHC II α and/or β polypeptide may be encoded by nucleotide sequences of HLA alleles known to be associated with common human diseases. Such HLA alleles include, but are not limited to, HLA-DRB1*0401, -DRB1*0301, -DQA1*0501, -DQB1*0201, -DRB1*1501, -DRB1*1502, -DQB1*0602, -DQA1*0102, -DQA1*0201, -DQB1*0202, -DQA1*0501, and combinations thereof. For a summary of HLA allele/disease associations, see Bakker et al. (2006), supra, incorporated herein by reference.

In one aspect, the non-human portion of a chimeric human/non-human MHC I, MHC II α and/or MHC II β polypeptide(s) comprises transmembrane and/or cytoplasmic domains of an endogenous non-human (e.g., rodent, e.g., mouse, rat, etc.) MHC I, MHC II α and/or MHC II β polypeptide(s), respectively. Thus, the non-human portion of the chimeric human/non-human MHC I polypeptide may comprise transmembrane and/or cytoplasmic domains of an endogenous non-human MHC I polypeptide. The non-human portion of a chimeric MHC II α polypeptide may comprise transmembrane and/or cytoplasmic domains of an endogenous non-human MHC II α polypeptide. The non-human portion of a chimeric human/non-human MHC II β polypeptide may comprise transmembrane and/or cytoplasmic domains of an endogenous non-human MHC II β polypeptide. In one aspect, the non-human animal is mouse, and a non-human portion of the chimeric MHC I polypeptide is derived from a mouse H-2K protein. In one aspect, the animal is a mouse, and non-human portions of the chimeric MHC II α and β polypeptides are derived from a mouse H-2E protein. Thus, a non-human portion of the chimeric MHC I polypeptide may comprise transmembrane and cytoplasmic domains derived from a mouse H-2K, and non-human portions of the chimeric MHC II α and β polypeptides may comprise transmembrane and cytoplasmic domains derived from a mouse H-2E protein. Although specific H-2K and H-2E sequences are contemplated in the Examples, any suitable sequences, e.g., polymorphic variants, conservative/non-conservative amino acid substitutions, etc., are encompassed herein.

A chimeric human/non-human polypeptide may be such that it comprises a human or a non-human leader (signal) sequence. In one embodiment, the chimeric MHC I polypeptide comprises a non-human leader sequence of an endogenous MHC I polypeptide. In one embodiment, the chimeric MHC II α polypeptide comprises a non-human leader sequence of an endogenous MHC II α polypeptide. In one embodiment, the chimeric MHC II β polypeptide comprises a non-human leader sequence of an endogenous MHC II β polypeptide. In an alternative embodiment, the chimeric MHC I, MHC II α and/or MHC II β polypeptide(s) comprises a non-human leader sequence of MHC I, MHC II α and/or MHC II β polypeptide(s), respectively, from another non-human animal, e.g., another rodent or another mouse strain. Thus, the nucleotide sequence encoding the chimeric MHC I, MHC II α and/or MHC II β polypeptide may be operably linked to a nucleotide sequence encoding a non-human MHC I, MHC II α and/or MHC II β leader sequence, respectively. In yet another embodiment, the chimeric MHC I, MHC II α and/or MHC II β polypeptide(s) comprises a human leader sequence of human MHC I, human MHC II α and/or human MHC II β polypeptide, respectively (e.g., a leader sequence of human HLA-A2, human HLA-DRA and/or human HLA-DRβ1*04, respectively).

A chimeric human/non-human MHC I, MHC II α and/or MHC II β polypeptide may comprise in its human portion a complete or substantially complete extracellular domain of a human MHC I, human MHC II α and/or human MHC II β polypeptide, respectively. Thus, a human portion may comprise at least 80%, preferably at least 85%, more preferably at least 90%, e.g., 95% or more of the amino acids encoding an extracellular domain of a human MHC I, human MHC II α and/or human MHC II β polypeptide (e.g., human HLA-A2, human HLA-DRA and/or human HLA-DRβ1*04). In one example, substantially complete extracellular domain of the human MHC I, human MHC II α and/or human MHC II β polypeptide lacks a human leader sequence. In another example, the chimeric human/non-human MHC I, chimeric human/non-human MHC II α and/or the chimeric human/non-human MHC II β polypeptide comprises a human leader sequence.

Moreover, the chimeric MHC I, MHC II α and/or MHC II β polypeptide may be operably linked to (e.g., be expressed under the regulatory control of) endogenous non-human promoter and regulatory elements, e.g., mouse MHC I, MHC II α and/or MHC II β regulatory elements, respectively. Such arrangement will facilitate proper expression of the chimeric MHC I and/or MHC II polypeptides in the non-human animal, e.g., during immune response in the non-human animal.

The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the invention relates to a genetically modified mouse that comprises in its genome a first nucleotide sequence encoding a chimeric human/mouse MHC I, a second nucleotide sequence encoding a chimeric human/mouse MHC II α, and a third nucleotide sequence encoding a chimeric human/mouse MHC II β polypeptides. A human portion of the chimeric MHC I, MHC II α, and MHC II β may comprise an extracellular domain of a human MHC I, MHC II α, and MHC II β, respectively. In one embodiment, the mouse expresses functional chimeric human/mouse MHC I, MHC II α, and MHC II β polypeptides from its endogenous mouse MHC locus. In one embodiment, the mouse does not express functional mouse MHC polypeptides, e.g., functional mouse MHC I, MHC II α, and MHC II β polypeptides, from its endogenous mouse MHC locus.

In one embodiment, a human portion of the chimeric human/mouse MHC I polypeptide comprises a peptide binding domain or an extracellular domain of a human MHC I (e.g., human HLA-A, e.g., human HLA-A2, e.g., human HLA-A2.1). In some embodiments, the mouse does not express a peptide binding or an extracellular domain of an endogenous mouse MHC I polypeptide from its endogenous mouse MHC I locus. The peptide binding domain of the human MHC I may comprise α1 and α2 domains. Alternatively, the peptide binding domain of the human MHC I may comprise α1, α2, and α3 domains. In one aspect, the extracellular domain of the human MHC I comprises an extracellular domain of a human MHC I α chain. In one embodiment, the endogenous mouse MHC I locus is an H-2K (e.g., H-2Kb) locus, and the mouse portion of the chimeric MHC I polypeptide comprises transmembrane and cytoplasmic domains of a mouse H-2K (e.g., H-2Kb) polypeptide. Thus, in one embodiment, the mouse of the invention comprises at its endogenous mouse MHC I locus a nucleotide sequence encoding a chimeric human/mouse MHC I, wherein a human portion of the chimeric polypeptide comprises an extracellular domain of a human HLA-A2 (e.g., HLA-A2.1) polypeptide and a mouse portion comprises transmembrane and cytoplasmic domains of a mouse H-2K (e.g., H-2Kb) polypeptide, and a mouse expresses a chimeric human/mouse HLA-A2/H-2K protein. In other embodiment, the mouse portion of the chimeric MHC I polypeptide may be derived from other mouse MHC I, e.g., H-2D, H-2L, etc.; and the human portion of the chimeric MHC I polypeptide may be derived from other human MHC I, e.g., HLA-B, HLA-C, etc. In one aspect, the mouse does not express a functional H-2K polypeptide from its endogenous mouse H-2K locus.

In one embodiment, a human portion of the chimeric human/mouse MHC II α polypeptide comprises a human MHC II α peptide binding or extracellular domain and a human portion of the chimeric human/mouse MHC II β polypeptide comprises a human MHC II β peptide binding or extracellular domain. In some embodiments, the mouse does not express a peptide binding or an extracellular domain of endogenous mouse α and/or β polypeptide from an endogenous mouse locus (e.g., H-2A and/or H-2E locus). In some embodiments, the mouse comprises a genome that lacks a gene that encodes a functional MHC class II molecule comprising an H-2Ab1, H-2Aa, H-2Eb1, H-2Eb2, H-2Ea, and a combination thereof. The peptide-binding domain of the human MHC II α polypeptide may comprise α1 domain and the peptide-binding domain of the human MHC II β polypeptide may comprise a β1 domain; thus, the peptide-binding domain of the chimeric MHC II complex may comprise human α1 and β1 domains. The extracellular domain of the human MHC II α polypeptide may comprise α1 and α2 domains and the extracellular domain of the human MHC II β polypeptide may comprise β1 and β2 domains; thus, the extracellular domain of the chimeric MHC II complex may comprise human α1, α2, β1 and β2 domains. In one embodiment, the mouse portion of the chimeric MHC II complex comprises transmembrane and cytosolic domains of mouse MHC II, e.g. mouse H-2E (e.g., transmembrane and cytosolic domains of mouse H-2E α and β chains). Thus, in one embodiment, the mouse of the invention comprises at its endogenous mouse MHC II locus a nucleotide sequence encoding a chimeric human/mouse MHC II α, wherein a human portion of the chimeric MHC II α polypeptide comprises an extracellular domain derived from an α chain of a human MHC II (e.g., a chain of HLA-DR4) and a mouse portion comprises transmembrane and cytoplasmic domains derived from an α chain of a mouse MHC II (e.g., H-2E); and a mouse comprises at its endogenous mouse MHC II locus a nucleotide sequence encoding a chimeric human/mouse MHC II β, wherein a human portion of the chimeric MHC II β polypeptide comprises an extracellular domain derived from a β chain of a human MHC II (e.g., β chain of HLA-DR4) and a mouse portion comprises transmembrane and cytoplasmic domains derived from a β chain of a mouse MHC II (e.g., H-2E); wherein the mouse expresses a chimeric human/mouse HLA-DR4/H-2E protein. In other embodiment, the mouse portion of the chimeric MHC II protein may be derived from other mouse MHC II, e.g., H-2A, etc.; and the human portion of the chimeric MHC II protein may be derived from other human MHC II, e.g., HLA-DQ, etc. In one aspect, the mouse does not express functional endogenous H-2A and H-2E polypeptides from their endogenous mouse loci (e.g., the mouse does not express H-2Ab1, H-2Aa, H-2Eb1, H-2Eb2, and H-2Ea polypeptides).

In a further embodiment, a non-human animal of the invention, e.g., a rodent, e.g., a mouse, comprises at an endogenous β2 microglobulin locus a nucleotide sequence encoding a human or humanized β2 microglobulin. β2 microglobulin or the light chain of the MHC class I complex (also abbreviated "β2M") is a small (12 kDa) non-glycosylated protein, that functions primarily to stabilize the MHC I α chain. Generation of human or humanized microglobulin animals is described in detail in U.S. patent application Ser. No. 13/661,159, and is incorporated herein by reference. A mouse comprising a humanized MHC locus as described in the present disclosure, and a human or humanized β2 microglobulin locus as described in U.S. patent application Ser. No. 13/661,159, may be generated by any methods known in the art, e.g., breeding.

Various other embodiments of a genetically modified non-human animal, e.g. rodent, e.g., rat or mouse, would be evident to one skilled in the art from the present disclosure and from the disclosure of U.S. patent application Ser. Nos. 13/661,159 and 13/661,116, incorporated herein by reference.

In various aspects of the invention, the sequence(s) encoding a chimeric human/non-human MHC I and MHC II polypeptides are located at an endogenous non-human MHC locus (e.g., mouse H-2K and/or H-2E locus). In one embodiment, this results in a replacement of an endogenous MHC gene(s) or a portion thereof with a nucleotide sequence(s) encoding a human or humanized MHC I polypeptides. Since the nucleotide sequences encoding MHC I, MHC II α and MHC II β polypeptides are located in proximity to one another on the chromosome, in order to achieve the greatest success in humanization of both MHC I and MHC II in one animal, the MHC I and MHC II loci should be targeted sequentially. Thus, also provided herein are methods of generating a genetically modified non-human animal comprising nucleotide sequences encoding chimeric human/non-human MHC I, MHC II α and MHC II β polypeptides as described herein.

In some embodiments, the method utilizes a targeting construct made using VELOCIGENE® technology, introducing the construct into ES cells, and introducing targeted ES cell clones into a mouse embryo using VELOCIMOUSE® technology, as described in the Examples.

The nucleotide constructs used for generating non-human animals described herein are also provided. In one aspect, the nucleotide construct comprises: 5' and 3' non-human homology arms, a human DNA fragment comprising human MHC gene sequences (e.g., human HLA-A2 or human HLA-DR4 gene sequences), and a selection cassette flanked by recombination sites. In one embodiment, the human DNA fragment is a genomic fragment that comprises both introns and exons of a human MHC gene (e.g., human HLA-A2 or HLA-DR4 gene). In one embodiment, the non-human homology arms are homologous to a non-human MHC locus (e.g., MHC I or MHC II locus). Specific constructs are described in the Examples below (e.g., FIG. 6 for MHC II construct, MAID 1680; FIG. 8 for MHC I construct, MAID 1665), as well as in U.S. application Ser. Nos. 13/661,159 and 13/661,116, incorporated herein by reference.

A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo, Hyg, Pur, CM, Spec, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art. In one embodiment, the selection cassette is located at the 5' end the human DNA fragment. In another embodiment, the selection cassette is located at the 3' end of the human DNA fragment. In another embodiment, the selection cassette is located within the human DNA fragment. In another embodiment, the selection cassette is located within an intron of the human DNA fragment.

In one embodiment, the 5' and 3' non-human homology arms comprise genomic sequence at 5' and 3' locations, respectively, of an endogenous non-human (e.g., murine) MHC class I or class II gene locus (e.g., 5' of the first leader sequence and 3' of the α3 exon of the mouse MHC I gene, or upstream of mouse H-2Ab1 gene and downstream of mouse H-2Ea gene). In one embodiment, the endogenous MHC class I locus is selected from mouse H-2K, H-2D and H-2L. In a specific embodiment, the endogenous MHC class I locus is mouse H-2K. In one embodiment, the endogenous MHC II locus is selected from mouse H-2E and H-2A. In one embodiment, the engineered MHC II construct allows replacement of both mouse H-2E and H-2A genes.

Thus, in one embodiment, provided herein is a method of generating a genetically engineered non-human animal (e.g., rodent, e.g., rat or mouse) capable of expressing humanized MHC I and II proteins comprising replacing at an endogenous non-human MHC II locus a nucleotide sequence encoding a non-human MHC II complex with a nucleotide sequence encoding a chimeric human/non-human MHC II complex to generate a first non-human animal; and replacing at an endogenous non-human MHC I locus a nucleotide sequence encoding a non-human MHC I polypeptide with a nucleotide sequence encoding a chimeric human/non-human MHC I polypeptide to generate a second non-human animal. In one embodiment, the steps of replacing nucleotide sequences comprise homologous recombination in ES cells. In one embodiment, the second non-human animal is generated by homologous recombination in ES cells bearing nucleotide sequences encoding chimeric human/non-human MHC II complex. Alternatively, also provided herein is a method of generating a genetically engineered non-human animal (e.g., rodent, e.g., rat or mouse) capable of expressing humanized MHC I and II proteins comprising replacing at an endogenous non-human MHC I locus a nucleotide sequence encoding a non-human MHC I polypeptide with a nucleotide sequence encoding a chimeric human/non-human MHC I polypeptide to generate a first non-human animal; and replacing at an endogenous non-human MHC II locus a nucleotide sequence encoding a non-human MHC II complex with a nucleotide sequence encoding a chimeric human/non-human MHC II complex to generate a second non-human animal. In such embodiment, the second non-human animal is generated by homologous recombination in ES cells bearing a nucleotide sequence encoding chimeric human/non-human MHC I polypeptide.

Upon completion of gene targeting, ES cells or genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCT (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

In one aspect, a cell that expresses a chimeric human/non-human MHC I and MHC II proteins (e.g., HLA-A2/H-2K and HLA-DR4/H-2E proteins) is provided. In one embodiment, the cell comprises an expression vector comprising a chimeric MHC class I sequence and chimeric MHC class II sequence as described herein. In one embodiment, the cell is selected from CHO, COS, 293, HeLa, and a retinal cell expressing a viral nucleic acid sequence (e.g., a PERC.6™ cell).

A chimeric MHC II complex comprising an extracellular domain of HLA-DR4 described herein maybe detected by anti-HLA-DR antibodies. Thus, a cell displaying chimeric human/non-human MHC II polypeptide may be detected and/or selected using anti-HLA-DR antibody. The chimeric MHC I complex comprising an extracellular domain of HLA-A2 described herein may be detected using anti-HLA-A, e.g., anti-HLA-A2 antibodies. Thus, a cell displaying a chimeric human/non-human MHC I polypeptide may be detected and/or selected using anti-HLA-A antibody. Antibodies that recognize other HLA alleles are commercially available or can be generated, and may be used for detection/selection.

Although the Examples that follow describe a genetically engineered animal whose genome comprises a replacement of a nucleotide sequence encoding mouse H-2K, and H-2A and H-2E proteins with a nucleotide sequence encoding a chimeric human/mouse HLA-A2/H-2K and HLA-DR4/H-2E protein, respectively, one skilled in the art would understand that a similar strategy may be used to introduce chimeras comprising other human MHC I and II genes (other HLA-A, HLA-B, and HLA-C; and other HLA-DR, HLA-DP and HLA-DQ genes). Such animals comprising multiple chimeric human/non-human (e.g., human/rodent, e.g., human/mouse) MHC I and MHC II genes at endogenous MHC loci are also provided.

In various embodiments, the genetically modified non-human animals described herein make cells, e.g., APCs, with human or humanized MHC I and II on the cell surface and, as a result, present peptides as epitopes for T cells in a human-like manner, because substantially all of the components of the complex are human or humanized. The genetically modified non-human animals of the invention can be used to study the function of a human immune system in the humanized animal; for identification of antigens and antigen epitopes that elicit immune response (e.g., T cell epitopes, e.g., unique human cancer epitopes), e.g., for use in vaccine development; for evaluation of vaccine candidates and other vaccine strategies; for studying human autoimmunity; for studying human infectious diseases; and otherwise for devising better therapeutic strategies based on human MHC expression.

EXAMPLES

The invention will be further illustrated by the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1: Engineering a Chimeric Human/Mouse MHC II Locus and Generation of Chimeric MHC II Mice Example 1.1: Deletion of the Endogenous MHC Class II H-2A and H-2E Loci The targeting vector for introducing a deletion of the endogenous MHC class II H-2Ab1, H-2Aa, H-2Eb1, H-2Eb2, and H-2Ea genes was made using VELOCI-GENE® genetic engineering technology (see, e.g., U.S. Pat. No. 6,586,251 and Valenzuela et al., supra). Bacterial Artificial Chromosome (BAC) RP23-458i22 (Invitrogen) DNA was modified to delete the endogenous MHC class II genes H-2Ab1, H-2Aa, H-2Eb1, H-2Eb2, and H-2Ea.

Briefly, upstream and downstream homology arms were derived by PCR of mouse BAC DNA from locations 5' of the H-2Ab1 gene and 3' of the H-2Ea gene, respectively. As depicted in FIG. 5, these homology arms were used to make a cassette that deleted ~79 kb of RP23-458i22 comprising genes H-2Ab1, H-2Aa, H-2Eb1, H-2Eb2, and H-2Ea of the MHC class II locus by bacterial homologous recombination (BHR). This region was replaced with a hygromycin cassette flanked by lox66 and lox71 sites. The final targeting vector from 5' to 3' included a 34 kb homology arm comprising mouse genomic sequence 5' to the H-2Ab1 gene of the endogenous MHC class II locus, a 5' lox66 site, a hygromycin cassette, a 3' lox71 site and a 63 kb homology arm comprising mouse genomic sequence 3' to the H-2Ea gene of the endogenous MHC class II locus (MAID 5111, see FIG. 6).

The BAC DNA targeting vector (described above) was used to electroporate mouse ES cells to create modified ES cells comprising a deletion of the endogenous MHC class II locus. Positive ES cells containing a deleted endogenous MHC class II locus were identified by the quantitative PCR assay using TAQMAN™ probes (Lie and Petropoulos (1998) Curr. Opin. Biotechnology 9:43-48). The upstream region of the deleted locus was confirmed by PCR using primers 5111U F (CAGAACGCCAGGCTGTAAC; SEQ ID NO:1) and 5111U R (GGAGAGCAGGGTCAGTCAAC; SEQ ID NO:2) and probe 5111U P (CACCGCCACTCACAGCTCCTTACA; SEQ ID NO:3), whereas the downstream region of the deleted locus was confirmed using primers 5111D F (GTGGGCACCATCTTCATCATTC; SEQ ID NO:4) and 5111D R (CTTCCTTTCCAGGGTGTGACTC; SEQ ID NO:5) and probe 5111D P (AGGCCTGCGATCAGGTGGCACCT; SEQ ID NO:6). The presence of the hygromycin cassette from the targeting vector was confirmed using primers HYGF (TGCGGCCGATCTTAGCC; SEQ ID NO:7) and HYGR (TTGACCGATTCCTTGCGG; SEQ ID NO:8) and probe HYGP (ACGAGCGGGTTCGGCCCATTC; SEQ ID NO:9). The nucleotide sequence across the upstream deletion point (SEQ ID NO:10) included the following, which indicates endogenous mouse sequence upstream of the deletion point (contained within the parentheses below) linked contiguously to cassette sequence present at the deletion point: (TTTGTAAACA AAGTCTACCC AGAGACAGAT GACAGACTTC AGCTCCAATG CTGATTGGTT CCTCACTTGG GACCAACCCT) CTCGAGTACC GTTCGTATAA TGTATGCTAT ACGAAGTTAT ATGCATCCGG GTAGGGGAGG. The nucleotide sequence across the downstream deletion point (SEQ ID NO:11) included the following, which indicates cassette sequence contiguous with endogenous mouse sequence downstream of the deletion point (contained within the parentheses below): CCTCGACCTG CAGCCCTAGG ATAACTTCGT ATAATGTATG CTATACGAAC GGTAGAGCTC (CACAGGCATT TGGGTGGGCA GGGATGGACG GTGACTGGGA CAATCGGGAT GGAAGAGCAT AGAATGGGAG TTAGGGAAGA). Positive ES cell clones were then used to implant female mice using the VELOCIMOUSE® method (described below) to generate a litter of pups containing a deletion of the endogenous MHC class II locus.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses, Nature Biotech. 25(1):91-99). Mice bearing a deletion of H-2Ab1, H-2Aa, H-2Eb1, H-2Eb2, and H-2Ea genes in the endogenous MHC class II locus were identified by genotyping using a modification of allele assay (Valenzuela et al., supra) that detected the presence of the hygromycin cassette and confirmed the absence of endogenous MHC class II sequences.

Mice bearing a deletion of H-2Ab1, H-2Aa, H-2Eb1, H-2Eb2, and H-2Ea genes in the endogenous MHC class II locus can be bred to a Cre deletor mouse strain (see, e.g., International Patent Application Publication No. WO 2009/114400) in order to remove any foxed hygromycin cassette introduced by the targeting vector that is not removed, e.g., at the ES cell stage or in the embryo. Optionally, the hygromycin cassette is retained in the mice.

Figure 5A:
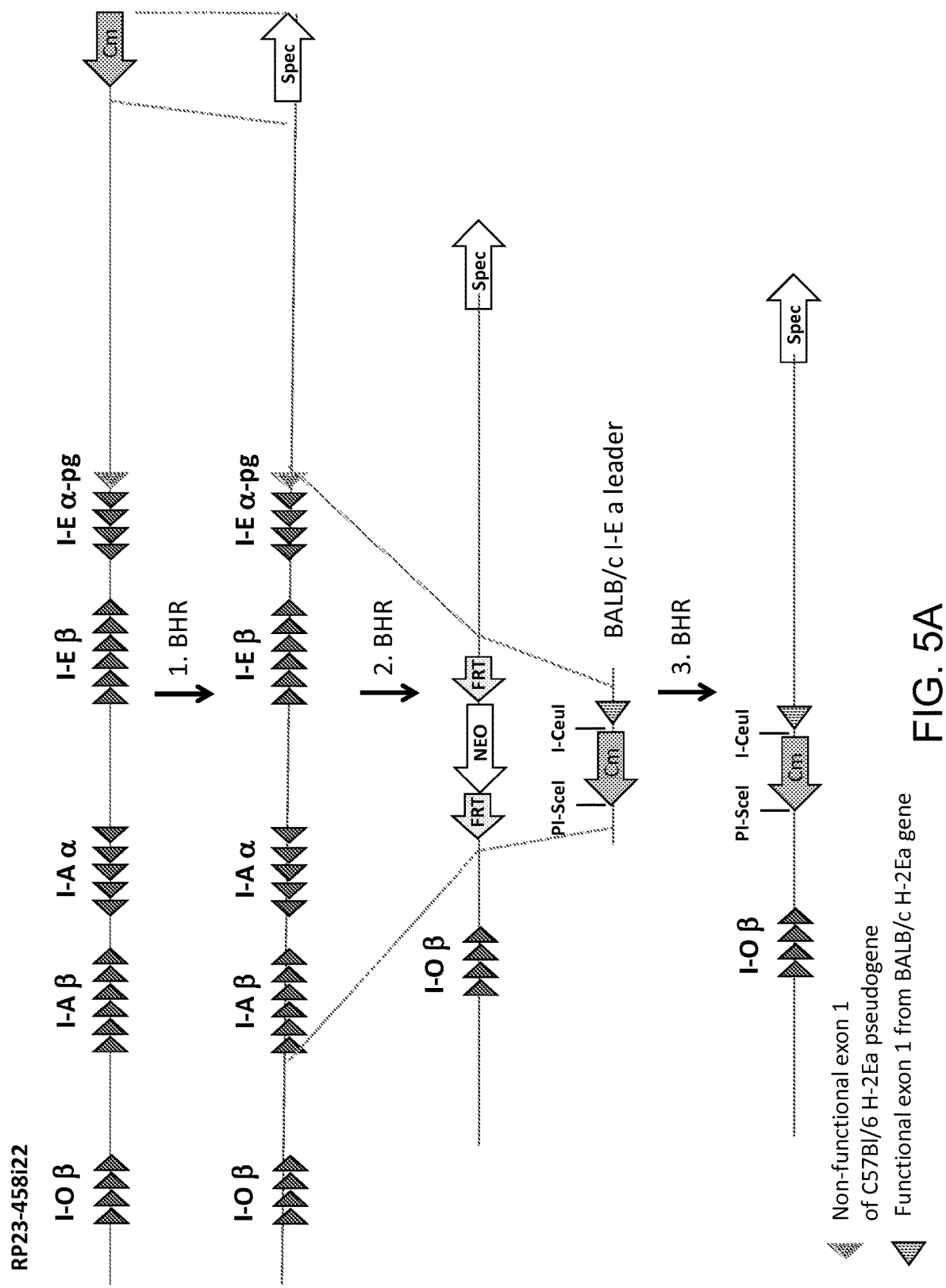
FIG. 5(A-D) is a schematic illustration (not to scale) of the strategy for generating a targeting vector comprising humanized I-E β and I-E α (i.e., H-2Eβ/HLA-DRβ1*04 and H-2Eα/HLA-DRα*01 chimera, respectively).
In FIG. 5C, the final humanized MHC II sequence from FIG. 5B is ligated between PI-SceI and I-CeuI restriction sites of the final construct from FIG. 5A, to generate a construct comprising humanized MHC II and exon 1 of I-Eα from BALB/c. Pg=pseudogene; BHR=bacterial homologous recombination; CM=chloramphenicol; spec=spectinomycin; hyg=hygromycin; neo=neomycin.
Figure 5B:
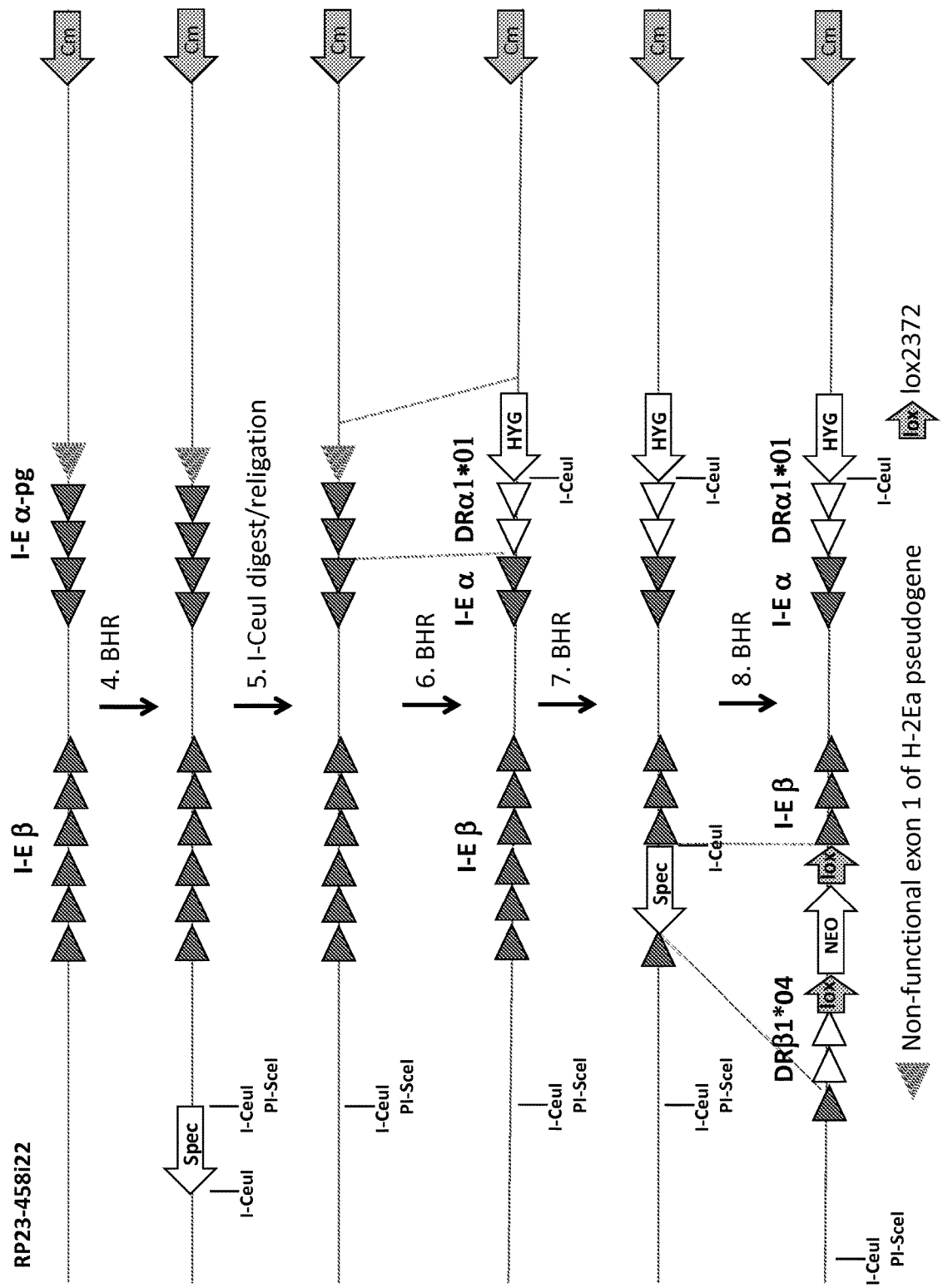

Example 1.2: Generation of Large Targeting Vector (LTVEC) Comprising Humanized H-2Eb1 and H-2Ea Genes A targeting vector to introduce humanized MHC II sequences was designed as depicted in FIG. 5. Using VELOCIGENE® genetic engineering technology, Bacterial Artificial Chromosome (BAC) RP23-458i22 DNA was modified in various steps to: (1) create a vector comprising a functional I-E α exon 1 from BALB/c H-2Ea gene (FIG. 5A); (2) create a vector comprising replacement of exons 2 and 3 of mouse I-E β gene with those of human DRβ1*04 and replacement of exons 2 and 3 of mouse I-E α with those of human DRα1*01 (FIG. 5B); (3) create a vector carrying exons 2 and 3 of human DRβ1*04 amongst remaining mouse I-E β exons, and exons 2 and 3 of human DRα1*01 amongst remaining mouse I-E α exons including a functional I-E α exon 1 from BALB/c mouse (step (1) (FIG. 5C); and (4) remove a cryptic splice site in the vector generated in (3) (FIG. 5D).

Specifically, because in the C57Bl/6 mice, the I-E α gene is a pseudogene due to the presence of a non-functional exon 1, first, a vector comprising a functional I-E α exon 1 from BALB/c H-2Ea gene was created (FIG. 5A). RP23-458i22 BAC was modified by bacterial homologous recombination (1.BHR) to replace chloramphenicol resistance gene with that of spectinomycin. The resultant vector was further modified by BHR to replace the entire I-A and I-E coding region with a neomycin cassette flanked by recombination sites (2.BHR). Another round of BHR (3. BHR) with the construct comprising an exon encoding BALB/c I-Eα leader (exon 1) and chloramphenicol gene flanked by PI-SceI and I-CeuI restriction sites resulted in a vector comprising a functional BALB/c H-2Ea exon 1.

Independently, in order to generate a vector comprising replacement of exons 2 and 3 of mouse I-E β gene with those of human DRβ1*04 and replacement of exons 2 and 3 of mouse I-E α with those of human DRα1*01, RP23-458i22 BAC was modified via several homologous recombination steps, 4. BHR-8. BHR (FIG. 5B). The resultant nucleic acid sequence was flanked by PI-SceI/I-CeuI restriction sites to allow ligation into the construct carrying BALB/c I-Eα exon 1, mentioned above (FIG. 5C).

Figure 5C:
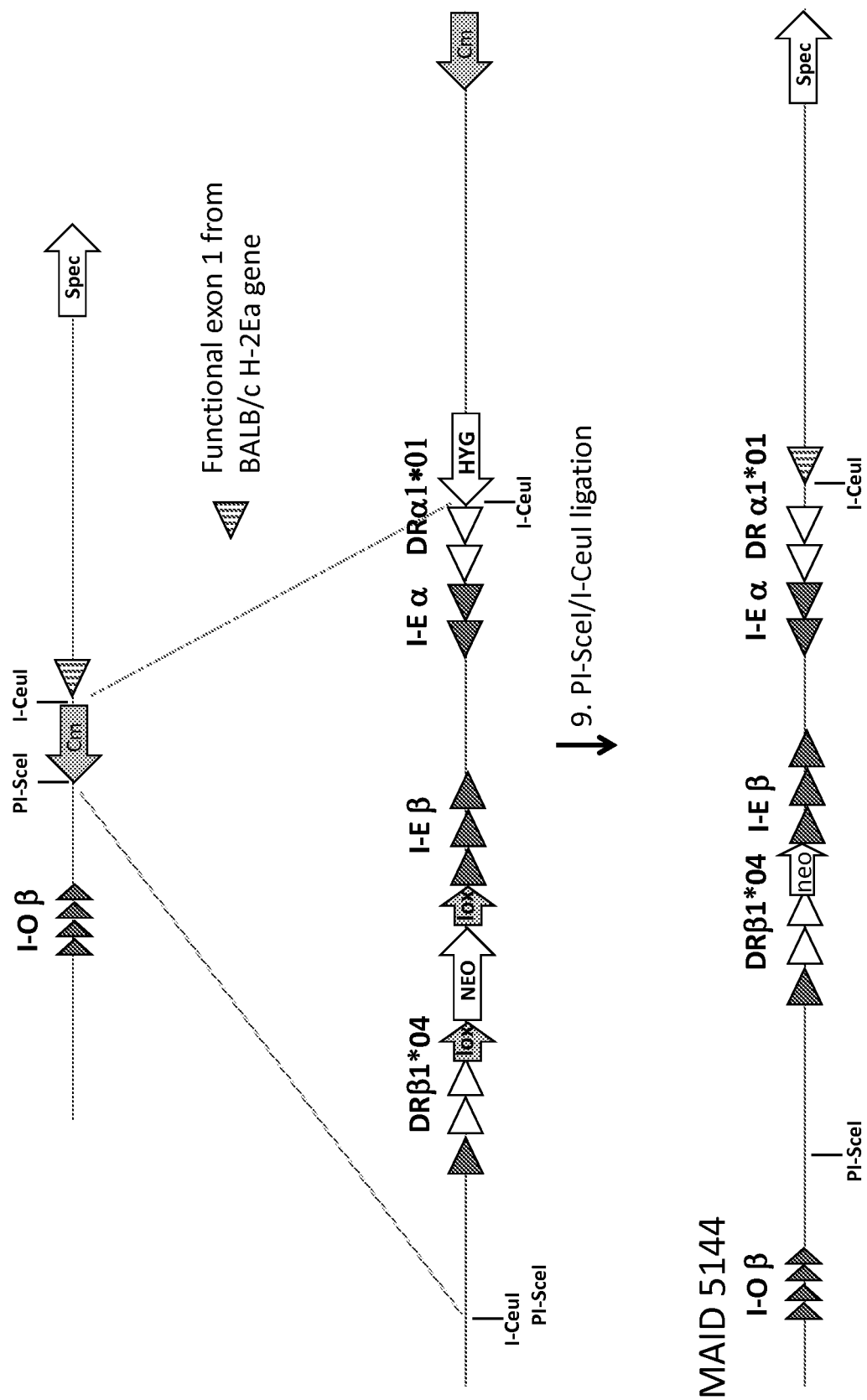
Figure 5D:
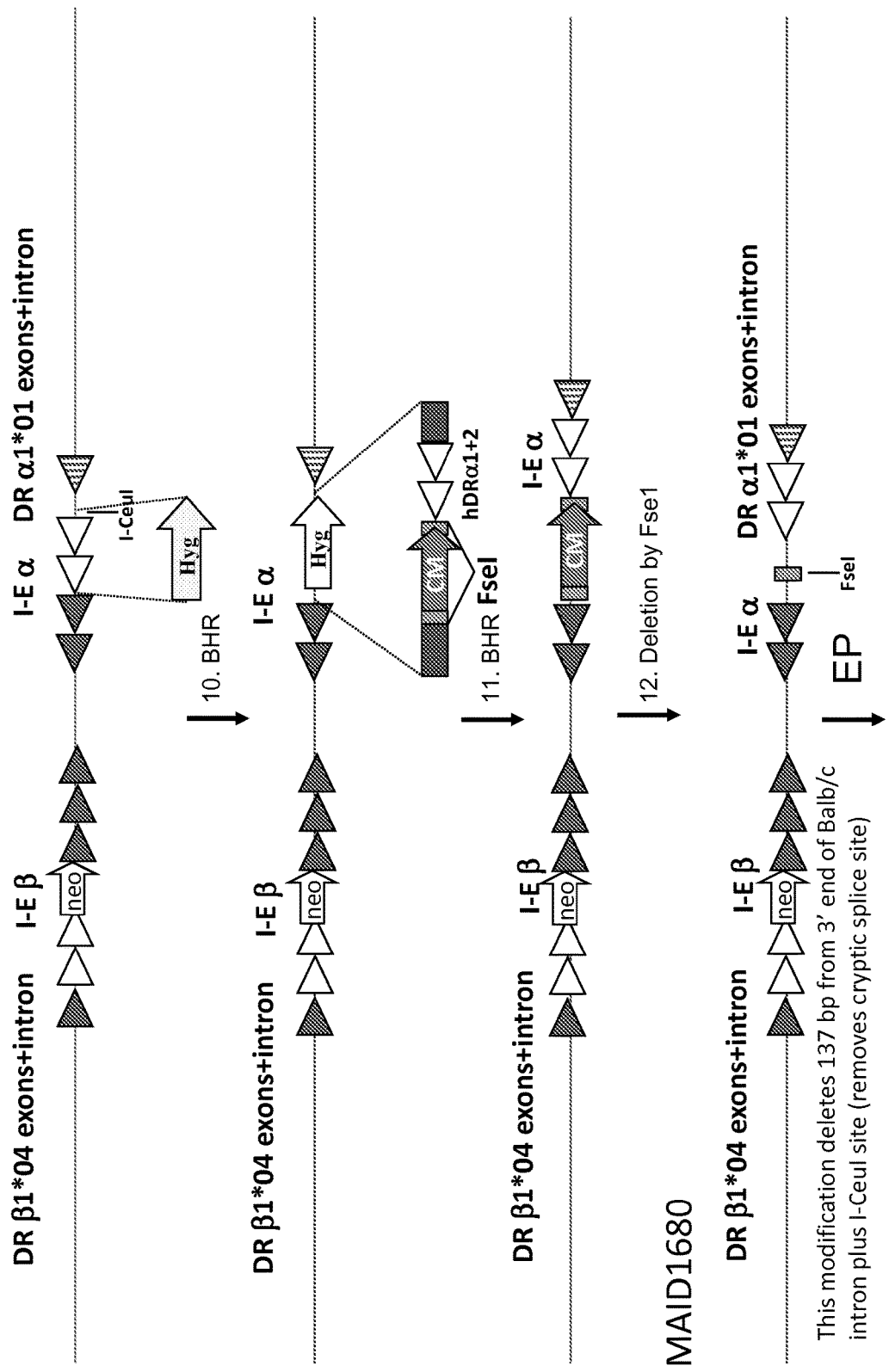

The sequence of the final construct depicted in FIG. 5C contained a cryptic splice site at the 3' end of the BALB/c intron. Several BHR steps (11. BHR-12. BHR) followed by a deletion step were performed to obtain the final targeting vector (MAID 1680) that was used to electroporate into ES cells (FIG. 5D).

In detail, the final targeting vector (MAID 1680), from 5' to 3', was comprised of a 5' mouse homology arm consisting of ~26 kb of mouse genomic sequence ending just upstream of the H-2Ab1 gene of the endogenous MHC class II locus; an ~59 kb insert containing the humanized MHC II β chain gene (humanized H-2Eb1 gene) and humanized MHC II α chain gene (humanized H-2Ea gene) and a floxed neomycin cassette; and a 3' mouse homology arm consisting of ~57 kb of mouse genomic sequence beginning just downstream of the H-2Ea gene of the endogenous MHC class II locus. The nucleotide sequence across the junction between the 5' arm and the insert (SEQ ID NO:12) included the following: (TGCTGATTGG TTCCTCACTT GGGACCAACC C) TAAGCTTTA TCTATGTCGG GTGCGGAGAA AGAGGTAATG AAATGGCACA AGGAGATCAC ACACCCAAAC CAAACTCGCC, where the italicized sequence is a unique PI-SceI site, and mouse genomic sequence in the 5' homology arm is in parentheses. The nucleotide sequence across the junction between the insert and the 3' arm (SEQ ID NO:13) included the following: CACATCAGTG AGGCTAGAAT AAATTAAAAT CGCTAATATG AAAATGGGG (ATTTGTACCT CTGAGTGTGA AGGCTGGGAA GACTGCTTTC AAGGGAC), where the mouse genomic sequence in the 3' homology arm is in parentheses.

Within the ~59 kb insert, the H-2Eb1 gene was modified as follows: a 5136 bp region of H-2Eb1, including the last 153 bp of intron1, exon 2, intron 2, exon 3, and the first 122 bp of intron 3, was replaced with the 3111 bp homologous region of human HLA-DRB1*04, including the last 148 bp of intron 1, exon 2, intron 2, exon 3, and the first 132 bp of intron 3. At the junction between the human and mouse sequences of intron 3, a cassette consisting of a 5' lox2372 site, UbC promoter, neomycin resistance gene, and a 3' lox2372 site, was inserted. The resulting gene encoded a chimeric HLA-DRB1*04/H-2Eb1 protein comprised of the mouse H-2Eb1 leader, the human β1 and β2 domains from DRB1*04, and the mouse transmembrane domain and cytoplasmic tail. The nucleotide sequence across the mouse/human junction in intron 1 (SEQ ID NO:14) included the following: (TCCATCACTT CACTGGGTAG CACAGCTGTA ACTGTCCAGC CTG) GGTACCGAGC TCGGATCCAC TAGTAACGGC CGCCAGTGTG CTGGAATTC GCCCTTGATC GAGCTCCCTG GGCTGCAGGT GGTGGGCGTT GCGGGTGGGG CCGGTTAA, where the italicized sequence is a multiple cloning site introduced during the cloning steps, and the mouse intron 1 sequences are in parentheses. The nucleotide sequence across the junction between the human intron 3 and neomycin cassette (SEQ ID NO:15) included the following: (ATCTCCATCA GAAGGGCACC GGT) ATAACTT CGTATAAGGT ATCCTATACG AAGTTATATG CATGGCCTCC GCGCCGGGTT, where the 5' lox2372 site is italicized, and human intron 3 sequence is in parentheses. The nucleotide sequence across the junction between the neomycin cassette and mouse intron 3 (SEQ ID NO:16) included the following: ATAACTTCGT ATAAGGTATC CTATACGAAG TTATCTCGAG (TGGCTTACAG GTAGGTGCGT GAAGCTTCTA CAAGCACAGT TGCCCCCTGG), where the 3' lox2372 site is italicized, and the mouse intron 3 sequence is in parentheses.

Also within the ~59 kb insert, the H-2Ea gene was modified as follows: a 1185 bp region of H-2Ea, including the last 101 bp of intron1, exon 2, intron 2, exon 3, and the first 66 bp of intron 3, was replaced with the 1189 bp homologous region of human HLA-DRA1*01, including the last 104 bp of intron 1, exon 2, intron 2, exon 3, and the first 66 bp of intron 3. As described above, because exon 1 of the C57BL/6 allele of H-2Ea contains a deletion which renders the gene nonfunctional, H-2Ea exon 1 and the remainder of intron 1 were replaced with the equivalent 2616 bp region from the BALB/c allele of H-2Ea, which is functional. The resulting gene encoded a chimeric H-2Ea/HLA-DRA1*01 protein comprised of the mouse H-2Ea leader from BALB/c, the human α1 and α2 domains from DRA1*01, and the mouse transmembrane domain and cytoplasmic tail. The nucleotide sequence across the mouse/human junction in intron 1 (SEQ ID NO:17) included the following: (CTGTTTCTTC CCTAACTCCC ATTCTATGCT CTTCCATCCC GA) CCGCGGCCCA ATCTCTCTCC ACT- ACTTCCT GCCTACATGT ATGTAGGT, where the italicized sequence is a restriction enzyme site introduced during the cloning steps, and the BALB/c intron 1 sequences are in parentheses. The nucleotide sequence across the human/mouse junction in intron 3 (SEQ ID NO:18) included the following: CAAGGTTTCC TCCTATGATG CTTGTGTGAA ACTCGGGGCC GGCC (AGCATTTAAC AGTACAGGGA TGGGAGCACA GCTCAC), where the italicized sequence is a restriction enzyme site introduced during the cloning steps, and the mouse intron 3 sequences are in parentheses. The nucleotide sequence across the C57BL/6-BALB/c junction 5' of exon 1 (SEQ ID NO:19) included the following: (GAAAGCAGTC TTCCCAGCCT TCACACTCAG AGGTACAAAT) CCCCATTTTC ATATTAGCGA TTTTAATTTA TTCTAGCCTC, where the C57BL/6-specific sequences are in parentheses. The nucleotide sequence across the BALB/c-C57BL/6 junction 3' of exon 1 (SEQ ID NO:20) included the following: TCTTCCCTAA CTCCCATTCT ATGCTCTTCC ATCCCGA CCG CGG (CCCAATC TCTCTCCACT ACTTCCTGCC TACATGTATG), where SacII restriction site is italicized, and C57BL/6 sequences are in parenthesis.

Example 1.3: Generation of Humanized MHC II Mice

Simplified diagrams of the strategy for generating humanized MHC II mice using the vector of Example 1.2 are presented in FIG. 6.

Specifically, MAID1680 BAC DNA (described above) was used to electroporate MAID5111 ES cells to create modified ES cells comprising a replacement of the endogenous mouse I-A and I-E loci with a genomic fragment comprising a chimeric human DR4/mouse I-E locus. Positive ES cells containing deleted endogenous I-A and I-E loci replaced by a genomic fragment comprising a chimeric human DR4/mouse I-E locus were identified by a quantitative PCR assay using TAQMAN™ probes (Lie and Petropoulos, supra). The insertion of the human DRα sequences was confirmed by PCR using primers hDRA1F (CTGGCGGCTTGAAGAATTTGG; SEQ ID NO:21), hDRA1R (CATGATTTCCAGGTTGGCTTTGTC; SEQ ID NO:22), and probe hDRA1P (CGATTTGCCAGCTTTGAGGCTCAAGG; SEQ ID NO:23). The insertion of the human DRβ sequences was confirmed by PCR using primers hDRB1F (AGGCTTGGGTGCTCCACTTG; SEQ ID NO:24), hDRB1R (GACCCTGGTGATGCTGGAAAC; SEQ ID NO:25), and probe hDRB1P (CAGGTGTAAACCTCTCCACTCCGAGGA; SEQ ID NO:26). The loss of the hygromycin cassette from the targeting vector was confirmed with primers HYGF (TGCGGCCGATCTTAGCC; SEQ ID NO:7) and HYGR (TTGACCGATTCCTTGCGG; SEQ ID NO:8) and probe HYGP (ACGAGCGGGTTCGGCCCATTC; SEQ ID NO:9).

Positive ES cell clones were then used to implant female mice using the VELOCIMOUSE® method (supra) to generate a litter of pups containing a replacement of the endogenous I-A and I-E loci with a chimeric human DR4/mouse I-E locus. Targeted ES cells described above were used as donor ES cells and introduced into an 8-cell stage mouse embryo by the VELOCIMOUSE® method. Mice bearing a chimeric human DR4/mouse I-E locus were identified by genotyping using a modification of allele assay (Valenzuela et al., supra) that detected the presence of a chimeric human DR4/mouse I-E locus.

Mice bearing a chimeric human DR4/mouse I-E locus can be bred to a Cre deletor mouse strain (see, e.g., International Patent Application Publication No. WO 2009/114400) in order to remove any foxed neomycin cassette introduced by the targeting vector that is not removed, e.g., at the ES cell stage or in the embryo (See FIG. 7).

Example 2: Engineering a Chimeric Human/Mouse MHC I Locus and Generation of Chimeric MHC I Mice The mouse H-2K gene was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al. (2003) High-throughput engineering of the mouse genome coupled with high-resolution expression analysis. Nat. Biotech. 21(6): 652-659). DNA from mouse BAC clone RP23-173k21 (Invitrogen) was modified by homologous recombination to replace the genomic DNA encoding the α1, α2 and α3 domains of the mouse H-2K gene with human genomic DNA encoding the α1, α2 and α3 subunits of the human HLA-A gene (FIG. 8).

Briefly, the genomic sequence encoding the mouse the α1, α2 and α3 subunits of the H-2K gene is replaced with the human genomic DNA encoding the α1, α2 and α3 domains of the human HLA-A*0201 gene in a single targeting event using a targeting vector comprising a hygromycin cassette flanked by loxP sites with a 5' mouse homology arm containing sequence 5' of the mouse H-2K locus including the 5' untranslated region (UTR; 5' homology arm is set forth in SEQ ID NO:27) and a 3' mouse homology arm containing genomic sequence 3' of the mouse H-2K α3 coding sequence (3' homology arm is set forth in SEQ ID NO:28).

The final construct for targeting the endogenous H-2K gene locus from 5' to 3' included (1) a 5' homology arm containing ~200 bp of mouse genomic sequence 5' of the endogenous H-2K gene including the 5'UTR, (2) ~1339 bp of human genomic sequence including the HLA-A*0201 leader sequence, the HLA-A*0201 leader/α1 intron, the HLA-A*0201 α1 exon, the HLA-A*0201 α1-α2 intron, the HLA-A*0201 α2 exon, ~316 bp of the 5' end of the α2-α3 intron, (3) a 5' loxP site, (4) a hygromycin cassette, (5) a 3' loxP site, (6) ~580 bp of human genomic sequence including ~304 bp of the 3' end of the α2-α3 intron, the HLA-A*0201 α3 exon, and (7) a 3' homology arm containing ~200 bp of mouse genomic sequence including the intron between the mouse H-2K α3 and transmembrane coding sequences (see FIG. 8 for schematic representation of the H-2K targeting vector). The sequence of 149 nucleotides at the junction of the mouse/human sequences at the 5' of the targeting vector is set forth in SEQ ID NO:29, and the sequence of 159 nucleotides at the junction of the human/mouse sequences at the 3' of the targeting vector is set forth in SEQ ID NO:30. Homologous recombination with this targeting vector created a modified mouse H-2K locus containing human genomic DNA encoding the α1, α2 and α3 domains of the HLA-A*0201 gene operably linked to the endogenous mouse H-2K transmembrane and cytoplasmic domain coding sequences which, upon translation, leads to the formation of a chimeric human/mouse MHC class I protein.

The targeted BAC DNA was used to electroporate mouse F1H4 ES cells to create modified ES cells for generating mice that express a chimeric MHC class I protein on the surface of nucleated cells (e.g., T and B lymphocytes, macrophages, neutrophils). ES cells containing an insertion of human HLA sequences were identified by a quantitative TAQMAN™ assay. Specific primer sets and probes were designed for detecting insertion of human HLA sequences and associated selection cassettes (gain of allele, GOA) and loss of endogenous mouse sequences (loss of allele, LOA). Table 2 identifies the names and locations detected for each of the probes used in the quantitative PCR assays.

TABLE 2

Probes Used For Genotyping

| Probe | Assay | Region Detected by Probe | Sequence | SEQ ID NO |
|---|---|---|---|---|
| HYG | GOA | Hygromycin cassette | ACGAGCGGGTTCGGCCCATTC | 9 |
| 1665H1 | GOA | Human HLA-A2 α2-α3 intron | AGTCCTTCAGCCTCCACTCAGGTCAGG | 31 |
| 1665H2 | GOA | Human HLA-A2 α2 exon | TACCACCAGTACGCCTACGACGGCA | 32 |
| 5112H2 | GOA | Human HLA-A2 α2-α3 intron | ATCCTGTACCAGAGAGTG | 33 |

The selection cassette may be removed by methods known by the skilled artisan. For example, ES cells bearing the chimeric human/mouse MHC class I locus may be transfected with a construct that expresses Cre in order to remove the "floxed" hygromycin cassette introduced by the insertion of the targeting construct containing human HLA-A*0201 gene sequences (See FIG. 8). The hygromycin cassette may optionally be removed by breeding to mice that express Cre recombinase. Optionally, the hygromycin cassette is retained in the mice.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) independently bearing a chimeric MHC class I gene were identified by genotyping using a modification of allele assay (Valenzuela et al., supra) that detects the presence of the unique human HLA-A*0201 gene sequences.

Example 3: Generation and Characterization of Mice Comprising Chimeric MHC I and MHC II Genes

Example 3.1: Generation of Mice Comprising Chimeric MHC I and II Genes

Figure 4:
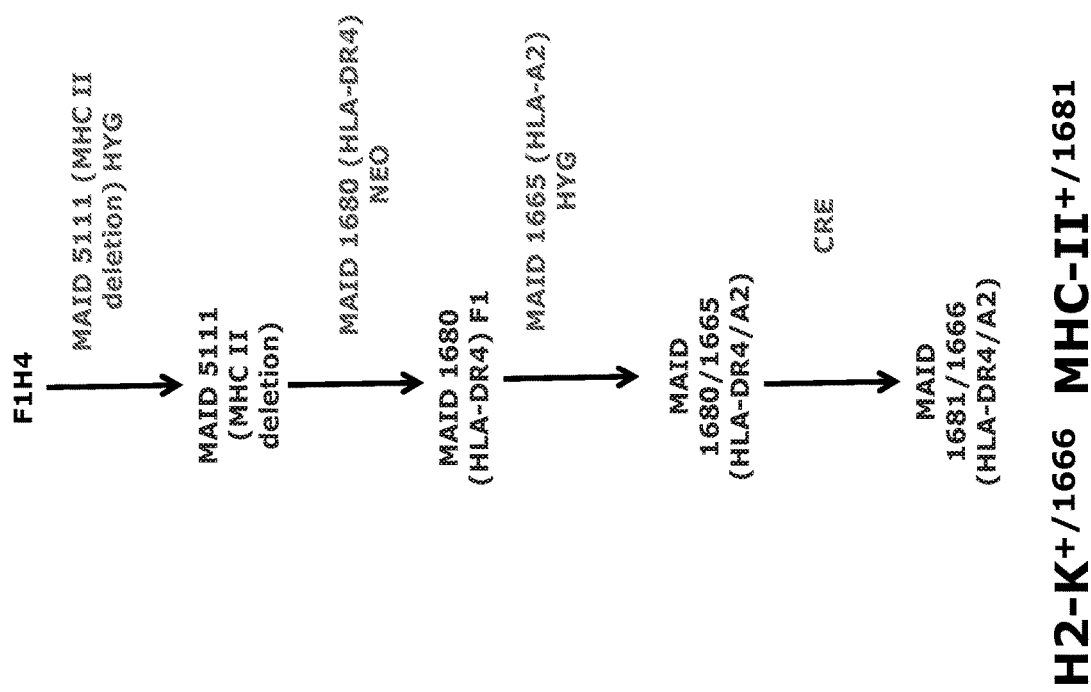
FIG. 4 depicts the strategy for generating a humanized MHC locus comprising humanized MHC I and MHC II genes. In the particular embodiment depicted, the MHC locus of the generated mouse comprises human HLA-A2 and HLA-DR4 sequences (H2-K$^{+/1666}$ MHC-II$^{+/1681}$). Large Targeting Vectors introduced into ES cells at each stage of humanization are depicted to the right of the arrows.

The strategy for generation of mice comprising chimeric MHC I and MHC II genes is depicted in FIG. 4. Specifically, MAID1665 BAC DNA (HLA-A2/H-2K BAC described above in Example 2) was used to electroporate MAID1680 ES cells (ES cells bearing a humanized MHC II gene described in Example 1) to create modified ES cells comprising chimeric human/mouse MHC I and MHC II genes. Positive ES cells containing both chimeric MHC I and II genes were identified by a quantitative PCR assay using TAQMAN™ probes (Lie and Petropoulos, supra) using primers and probes described in Examples 1 and 2 above.

The HYG and NEO selection cassettes may be removed by methods known by the skilled artisan. For example, ES cells bearing the chimeric human/mouse MHC class I and II loci may be transfected with a construct that expresses Cre in order to remove the "floxed" hygromycin and neomycin cassettes introduced by the insertion of the targeting constructs (see FIGS. 4, 7, and 8). The selection cassettes may optionally be removed by breeding to mice that express Cre recombinase. Optionally, the selection cassette is retained in the mice.

Targeted ES cells comprising both humanized MHC I and II described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) bearing a chimeric MHC class I and class II genes were identified by genotyping using a modification of allele assay (Valenzuela et al., supra).

Example 3.2: Characterization of Mice Comprising Chimeric MHC I and II Genes Spleens from WT or double heterozygous humanized HLA-A2/HLA-DR4 mice ("1666HET/1681 HET" or "H-2K$^{+/1666}$ MHC-II$^{+/1681}$") were perfused with Collagenase D (Roche Bioscience) and erythrocytes were lysed with ACK lysis buffer. Cell surface expression of human HLA-A2 and HLA-DR4 was analyzed by FACS using fluorochrome-conjugated anti-CD3 (17A2), anti-CD19 (1D3), anti-HLA-A2 (BB7.2) and anti-HLA-DR (L243). Flow cytometry was performed using BD-Fortessa. Expression of both human HLA-A2 and HLA-DR4 were clearly detectable on the surface of CD19+ B cells (FIG. 9).

EQUIVALENTS

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, patent applications and patents cited throughout this application are incorporated by reference herein in their entirety.

What is claimed is:

1. A genetically modified mouse cell comprising in its genome:
   (i) at an endogenous MHC I locus, a first nucleotide sequence comprising at least a part of a human MHC I gene that encodes α1, α2 and α3 domains of a classical human MHC I polypeptide and at least a part of a mouse MHC I gene that encodes transmembrane and cytoplasmic domains of a classical mouse MHC I polypeptide, such that the first nucleotide sequence encodes a chimeric human/mouse MHC I polypeptide that comprises the α1, α2 and α3 domains of the classical human MHC I polypeptide operably linked to the transmembrane and cytoplasmic domains of the classical mouse MHC I polypeptide,
   (ii) at an endogenous MHC II α locus, a second nucleotide sequence comprising at least a part of a human MHC II α gene that encodes an α2 domain of a classical human MHC II α polypeptide and at least a part of a mouse MHC II α gene that encodes transmembrane and cytoplasmic domains of a classical mouse MHC II α polypeptide, such that the second nucleotide sequence encodes a chimeric human/mouse MHC II α polypeptide that comprises the α2 domain of the classical human MHC II α polypeptide operably linked to the transmembrane and cytoplasmic domains of the classical mouse MHC II α polypeptide, and
   (iii) at an endogenous MHC II β locus, a third nucleotide sequence comprising at least a part of a human MHC II β gene that encodes a β2 domain of a classical human MHC II β polypeptide and at least a part of a mouse MHC II β gene that encodes transmembrane and cytoplasmic domains of a classical mouse MHC II β polypeptide, such that the third nucleotide sequence encodes a chimeric human/mouse MHC II β polypeptide that comprises the β2 domain of the classical human MHC II β polypeptide operably linked to the transmembrane and cytoplasmic domains of the classical mouse MHC II β polypeptide.

2. The mouse cell of claim 1, wherein the first, second and/or third nucleotide sequence(s) are operably linked to endogenous mouse regulatory elements.

3. The mouse cell of claim 1, wherein the classical human MHC I polypeptide is HLA-A or HLA-B.

4. The mouse cell of claim 1, further comprising at an endogenous mouse β2 microglobulin locus a nucleotide sequence encoding a human or humanized β2 microglobulin polypeptide.

5. The mouse cell of claim 1, wherein the first nucleotide sequence is operably linked to endogenous mouse MHC I promoter and regulatory elements at the endogenous MHC I locus, the second nucleotide sequence is operably linked to endogenous mouse MHC II α promoter and regulatory elements at the endogenous MHC II α locus, and the third nucleotide sequence is operably linked to endogenous mouse MHC II β promoter and regulatory elements at the endogenous MHC II β locus.

6. The mouse cell of claim 1, wherein the classical human MHC class II α and β polypeptides respectively are human HLA-DR α and β polypeptides or human HLA-DQ α and β polypeptides.

7. The mouse cell of claim 1, wherein the classical mouse MHC I polypeptide is H-2K or H-2D.

8. The mouse cell of claim 1, wherein the classical mouse MHC II α and β polypeptides respectively are H-2A α and β polypeptides.

9. The mouse cell of claim 1, wherein the classical mouse MHC II α and β polypeptides respectively are H-2E α and β polypeptides.

10. The mouse cell of claim 1, wherein the first nucleotide sequence encodes a chimeric HLA-A/H-2K polypeptide, the second nucleotide sequence encodes an α chain of a chimeric HLA-DR/H-2E polypeptide, and the third nucleotide sequence encodes a β chain of a chimeric HLA-DR/H-2E polypeptide, and wherein the mouse cell expresses the HLA-A/H-2K polypeptide and the HLA-DR/H-2E polypeptide.

11. The mouse cell of claim 10, wherein the mouse further comprises at an endogenous β2 microglobulin locus a nucleotide sequence encoding a human or humanized β2 microglobulin polypeptide.

12. The mouse cell of claim 11, wherein the mouse cell further does not express functional endogenous MHC polypeptides from the endogenous MHC loci.

13. The mouse of claim 1, wherein the chimeric human/mouse MHC II α polypeptide further comprises an α1 domain of the classical human MHC II α polypeptide and wherein the chimeric human/mouse MHC II β polypeptide further comprises a β1 domain of the classical human MHC II β polypeptide.

14. The mouse cell of claim 13, wherein the mouse cell is an antigen presenting cell (APC), and wherein the APC expresses on its surface the chimeric human/mouse MHC I polypeptide and a chimeric human/mouse MHC II complex comprising the chimeric human/mouse MHC II α and β polypeptides from the endogenous MHC loci.

15. The mouse cell of claim 14, further comprising at an endogenous mouse β2 microglobulin locus a nucleotide sequence encoding a human or humanized β2 microglobulin polypeptide, wherein the mouse cell expresses the human or humanized β2 microglobulin polypeptide.

16. The mouse cell of claim 1, wherein the cell is isolated from a genetically modified mouse whose genome comprises:
(i) at an endogenous MHC I locus, a first nucleotide sequence comprising at least a part of a human MHC I gene that encodes α1, α2 and α3 domains of a classical human MHC I polypeptide and at least a part of a mouse MHC I gene that encodes transmembrane and cytoplasmic domains of a classical mouse MHC I polypeptide, such that the first nucleotide sequence encodes a chimeric human/mouse MHC I polypeptide that comprises the α1, α2 and α3 domains of the classical human MHC I polypeptide operably linked to the transmembrane and cytoplasmic domains of the classical mouse MHC I polypeptide,
(ii) at an endogenous MHC II α locus, a second nucleotide sequence comprising at least a part of a human MHC II α gene that encodes an α2 domain of a classical human MHC II α polypeptide and at least a part of a mouse MHC II α gene that encodes transmembrane and cytoplasmic domains of a classical mouse MHC II α polypeptide, such that the second nucleotide sequence encodes a chimeric human/mouse MHC II α polypeptide that comprises the α2 domain of the classical human MHC II α polypeptide operably linked to the transmembrane and cytoplasmic domains of the classical mouse MHC II α polypeptide, and
(iii) at an endogenous MHC II β locus, a third nucleotide sequence comprising at least a part of a human MHC II β gene that encodes a β2 domain of a classical human MHC II β polypeptide and at least a part of a mouse MHC II β gene that encodes transmembrane and cytoplasmic domains of a classical mouse MHC II β polypeptide, such that the third nucleotide sequence encodes a chimeric human/mouse MHC II β polypeptide that comprises the β2 domain of the classical human MHC II β polypeptide operably linked to the transmembrane and cytoplasmic domains of the classical mouse MHC II β polypeptide,
wherein the mouse expresses the chimeric human/mouse MHC I polypeptide and a chimeric human/mouse MHC II complex comprising the chimeric human/mouse MHC II α and β polypeptides from the endogenous MHC loci.

17. The mouse cell of claim 1, wherein the mouse cell is an embryonic stem cell.

18. An embryo derived from the mouse cell of claim 1, wherein the embryo develops into a mouse that expresses from the endogenous MHC loci the chimeric human/mouse MHC I polypeptide and a chimeric human/mouse MHC II complex comprising the chimeric human/mouse MHC II α and β polypeptides.

19. A mouse tissue comprising the mouse cell of claim 1.

20. A genetically modified mouse embryonic stem cell comprising in its genome:
(i) at an endogenous MHC I locus, a first nucleotide sequence comprising at least a part of a human MHC I gene that encodes α1, α2 and α3 domains of a classical human MHC I polypeptide and at least a part of a mouse MHC I gene that encodes transmembrane and cytoplasmic domains of a classical mouse MHC I polypeptide, such that the first nucleotide sequence encodes a chimeric human/mouse MHC I polypeptide that comprises the α1, α2 and α3 domains of the classical human MHC I polypeptide operably linked to the transmembrane and cytoplasmic domains of the classical mouse MHC I polypeptide,
(ii) at an endogenous MHC II α locus, a second nucleotide sequence comprising at least a part of a human MHC II α gene that encodes an α2 domain of a classical human MHC II α polypeptide and at least a part of a mouse MHC II α gene that encodes transmembrane and cytoplasmic domains of a classical mouse MHC II α polypeptide, such that the second nucleotide sequence encodes a chimeric human/mouse MHC II α polypeptide that comprises the α1 and α2 domains of the classical human MHC II α polypeptide operably linked to the transmembrane and cytoplasmic domains of the classical mouse MHC II α polypeptide, and (iii) at an endogenous MHC II β locus, a third nucleotide sequence comprising at least a part of a human MHC II β gene that encodes a β2 domain of a classical human MHC II β polypeptide and at least a part of a mouse MHC II β gene that encodes transmembrane and cytoplasmic domains of a classical mouse MHC II β polypeptide, such that the third nucleotide sequence encodes a chimeric human/mouse MHC II β polypeptide that comprises the β1 and β2 domains of the classical human MHC II β polypeptide operably linked to the transmembrane and cytoplasmic domains of the classical mouse MHC II β polypeptide.

21. The mouse embryonic stem cell of claim 20, further comprising at an endogenous mouse β2 microglobulin locus a nucleotide sequence encoding a human or humanized β2 microglobulin polypeptide.

\* \* \* \* \*

UNITED STATES PATENT AND TRADEMARK OFFICE
CERTIFICATE OF CORRECTION

PATENT NO.         : 11,224,208 B2
APPLICATION NO.    : 16/184473
DATED              : January 18, 2022
INVENTOR(S)        : Lynn Macdonald et al.

It is certified that error appears in the above-identified patent and that said Letters Patent is hereby corrected as shown below:

In the Claims

Claim 13, Line 1, Column 43, Line 41:
The mouse of claim 1,
Should be:
--The mouse cell of claim 1,--

Claim 20, Line 17, Column 44, Line 60:
α gene that encodes an α2 domain of a classical human
Should be:
--α gene that encodes α1 and α2 domains of a classical human--

Claim 20, Line 29, Column 45, Line 5:
β gene that encodes a β2 domain of a classical human
Should be:
--β gene that encodes β1 and β2 domains of a classical human--

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 33

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
cagaacgcca ggctgtaac                                                    19

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
ggagagcagg gtcagtcaac                                                   20

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
caccgccact cacagctcct taca                                              24

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
gtgggcacca tcttcatcat tc                                                22

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
cttcctttcc agggtgtgac tc                                                22

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
aggcctgcga tcaggtggca cct                                               23

<210> SEQ ID NO 7
<211> LENGTH: 17
<212> TYPE: DNA
<213> ORGANISM: Artificial Sequence
<220> FEATURE:
<223> OTHER INFORMATION: Synthetic

<400> SEQUENCE: 7
tgcggccgat cttagcc                                                    17

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8
ttgaccgatt ccttgcgg                                                   18

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
acgagcgggt tcggcccatt c                                               21

<210> SEQ ID NO 10
<211> LENGTH: 140
<212> TYPE: DNA
<213> ORGANISM: Artificial Sequence
<220> FEATURE:
<223> OTHER INFORMATION: Synthetic

<400> SEQUENCE: 10
tttgtaaaca aagtctaccc agagacagat gacagacttc agctccaatg ctgattggtt     60
cctcacttgg gaccaaccct ctcgagtacc gttcgtataa tgtatgctat acgaagttat    120
atgcatccgg gtaggggagg                                                140

<210> SEQ ID NO 11
<211> LENGTH: 140
<212> TYPE: DNA
<213> ORGANISM: Artificial Sequence
<220> FEATURE:
<223> OTHER INFORMATION: Synthetic

<400> SEQUENCE: 11
cctcgacctg cagccctagg ataacttcgt ataatgtatg ctatacgaac ggtagagctc     60
cacaggcatt tgggtgggca gggatggacg gtgactggga caatcgggat ggaagagcat    120
agaatgggag ttagggaaga                                                140

<210> SEQ ID NO 12
<211> LENGTH: 110
<212> TYPE: DNA
<213> ORGANISM: Artificial Sequence
<220> FEATURE:
<223> OTHER INFORMATION: Synthetic

<400> SEQUENCE: 12
tgctgattgg ttcctcactt gggaccaacc ctaagcttta tctatgtcgg gtgcggagaa     60
agaggtaatg aaatggcaca aggagatcac acacccaaac caaactcgcc                110

<210> SEQ ID NO 13

<211> LENGTH: 96
<212> TYPE: DNA
<213> ORGANISM: Artificial Sequence
<220> FEATURE:
<223> OTHER INFORMATION: Synthetic

<400> SEQUENCE: 13

```
cacatcagtg aggctagaat aaattaaaat cgctaatatg aaaatgggga tttgtacctc    60
tgagtgtgaa ggctgggaag actgctttca agggac                              96
```

<210> SEQ ID NO 14
<211> LENGTH: 150
<212> TYPE: DNA
<213> ORGANISM: Artificial Sequence
<220> FEATURE:
<223> OTHER INFORMATION: Synthetic

<400> SEQUENCE: 14

```
tccatcactt cactgggtag cacagctgta actgtccagc ctgggtaccg agctcggatc    60
cactagtaac ggccgccagt gtgctggaat tcgcccttga tcgagctccc tgggctgcag   120
gtggtgggcg ttgcgggtgg ggccggttaa                                    150
```

<210> SEQ ID NO 15
<211> LENGTH: 80
<212> TYPE: DNA
<213> ORGANISM: Artificial Sequence
<220> FEATURE:
<223> OTHER INFORMATION: Synthetic

<400> SEQUENCE: 15

```
atctccatca gaagggcacc ggtataactt cgtataaggt atcctatacg aagttatatg    60
catggcctcc gcgccgggtt                                                80
```

<210> SEQ ID NO 16
<211> LENGTH: 90
<212> TYPE: DNA
<213> ORGANISM: Artificial Sequence
<220> FEATURE:
<223> OTHER INFORMATION: Synthetic

<400> SEQUENCE: 16

```
ataacttcgt ataaggtatc ctatacgaag ttatctcgag tggcttacag gtaggtgcgt    60
gaagcttcta caagcacagt tgcccccctgg                                    90
```

<210> SEQ ID NO 17
<211> LENGTH: 90
<212> TYPE: DNA
<213> ORGANISM: Artificial Sequence
<220> FEATURE:
<223> OTHER INFORMATION: Synthetic

<400> SEQUENCE: 17

```
ctgtttcttc cctaactccc attctatgct cttccatccc gaccgcggcc caatctctct    60
ccactacttc ctgcctacat gtatgtaggt                                     90
```

<210> SEQ ID NO 18
<211> LENGTH: 80
<212> TYPE: DNA
<213> ORGANISM: Artificial Sequence
<220> FEATURE:
<223> OTHER INFORMATION: Synthetic

<400> SEQUENCE: 18
caaggtttcc tcctatgatg cttgtgtgaa actcggggcc ggccagcatt taacagtaca    60
gggatgggag cacagctcac                                                80

<210> SEQ ID NO 19
<211> LENGTH: 80
<212> TYPE: DNA
<213> ORGANISM: Artificial Sequence
<220> FEATURE:
<223> OTHER INFORMATION: Synthetic

<400> SEQUENCE: 19
gaaagcagtc ttcccagcct tcacactcag aggtacaaat ccccattttc atattagcga    60 tttttaattta ttctagcctc                                                80

<210> SEQ ID NO 20
<211> LENGTH: 80
<212> TYPE: DNA
<213> ORGANISM: Artificial Sequence
<220> FEATURE:
<223> OTHER INFORMATION: Synthetic

<400> SEQUENCE: 20
tcttccctaa ctcccattct atgctcttcc atcccgaccg cggcccaatc tctctccact    60
acttcctgcc tacatgtatg                                                80

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ctggcggctt gaagaatttg g                                              21

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
catgatttcc aggttggctt tgtc                                           24

<210> SEQ ID NO 23
<211> LENGTH: 26
<212> TYPE: DNA
<213> ORGANISM: Artificial Sequence
<220> FEATURE:
<223> OTHER INFORMATION: Synthetic

<400> SEQUENCE: 23
cgatttgcca gctttgaggc tcaagg                                         26

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
aggcttgggt gctccacttg                                           20

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
gaccctggtg atgctggaaa c                                         21

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
caggtgtaaa cctctccact ccgagga                                   27

<210> SEQ ID NO 27
<211> LENGTH: 200
<212> TYPE: DNA
<213> ORGANISM: Artificial Sequence
<220> FEATURE:
<223> OTHER INFORMATION: Synthetic

<400> SEQUENCE: 27
ggattcccca tctccacagt ttcacttctg cacctaacct gggtcaggtc cttctgtccg    60
gacactgttg acgcgcagtc agctcttacc cccattgggt ggcgcgatca cccaagaacc   120
aatcagtgtc gccgcggacg ctggatataa agtccacgca gcccgcagaa ctcagaagtc   180
gcgaatcgcc gacaggtgcg                                              200

<210> SEQ ID NO 28
<211> LENGTH: 200
<212> TYPE: DNA
<213> ORGANISM: Artificial Sequence
<220> FEATURE:
<223> OTHER INFORMATION: Synthetic

<400> SEQUENCE: 28
gtaaggagag tgtgggtgca gagctggggt cagggaaagc tggagctttc tgcagaccct    60
gagctgctca gggctgagag ctggggtcat gaccctcacc ttcatttctt gtacctgtcc   120
ttcccagagc ctcctccatc cactgtctcc aacatggcga ccgttgctgt tctggttgtc   180
cttggagctg caatagtcac                                              200

<210> SEQ ID NO 29
<211> LENGTH: 149
<212> TYPE: DNA
<213> ORGANISM: Artificial Sequence
<220> FEATURE:
<223> OTHER INFORMATION: Synthetic

<400> SEQUENCE: 29
agtgtcgccg cggacgctgg atataaagtc cacgcagccc gcagaactca gaagtcgcga    60
atcgccgaca ggtgcgatgg ccgtcatggc gccccgaacc ctcgtcctgc tactctcggg   120
ggctctggcc ctgacccaga cctgggcgg                                    149

```
<210> SEQ ID NO 30
<211> LENGTH: 159
<212> TYPE: DNA
<213> ORGANISM: Artificial Sequence
<220> FEATURE:
<223> OTHER INFORMATION: Synthetic

<400> SEQUENCE: 30
ggtggtgcct tctggacagg agcagagata cacctgccat gtgcagcatg agggtttgcc      60
caagcccctc accctgagat ggggtaagga gagtgtgggt gcagagctgg ggtcagggaa     120
agctggagct ttctgcagac cctgagctgc tcagggctg                            159

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
agtccttcag cctccactca ggtcagg                                          27

<210> SEQ ID NO 32
<211> LENGTH: 25
<212> TYPE: DNA
<213> ORGANISM: Artificial Sequence
<220> FEATURE:
<223> OTHER INFORMATION: Synthetic

<400> SEQUENCE: 32
taccaccagt acgcctacga cggca                                            25

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
atcctgtacc agagagtg                                                    18
```